(12) United States Patent
Chen et al.

(10) Patent No.: US 7,989,441 B2
(45) Date of Patent: Aug. 2, 2011

(54) ORGANIC COMPOUNDS

(75) Inventors: Zhuoliang Chen, Belmont, MA (US); Mark G. Palermo, Rindge, NH (US); Sushil K. Sharma, West Orange, NJ (US); Troy Smith, Nashua, NH (US); Christopher S. Straub, Stow, MA (US); Run-Ming D. Wang, Somerville, MA (US); Yaping Wang, Boxborough, MA (US); Leigh Zawel, Hingham, MA (US)

(73) Assignee: Novartis AG, Basel (CH)

( * ) Notice: Subject to any disclaimer, the term of this patent is extended or adjusted under 35 U.S.C. 154(b) by 579 days.

(21) Appl. No.: 11/916,887

(22) PCT Filed: Jun. 6, 2006

(86) PCT No.: PCT/US2006/021850
§ 371 (c)(1),
(2), (4) Date: Aug. 5, 2008

(87) PCT Pub. No.: WO2006/133147
PCT Pub. Date: Dec. 14, 2006

(65) Prior Publication Data
US 2009/0069294 A1   Mar. 12, 2009

Related U.S. Application Data

(60) Provisional application No. 60/688,639, filed on Jun. 8, 2005.

(51) Int. Cl.
*A61K 31/44* (2006.01)
*C07D 223/12* (2006.01)
*C07D 211/76* (2006.01)

(52) U.S. Cl. ............... 514/211.03; 514/349; 540/527; 546/297

(58) Field of Classification Search ................ None
See application file for complete search history.

(56) References Cited

U.S. PATENT DOCUMENTS

| 5,521,179 A | 5/1996 | Bernstein et al. |
| 2004/0242494 A1 | 12/2004 | Brenchley et al. |

FOREIGN PATENT DOCUMENTS

| WO | WO 03/065987 A2 | 8/2003 |
| WO | WO 2004/072641 A1 | 8/2004 |
| WO | WO 2005/069894 A2 | 8/2005 |
| WO | WO 2006/010118 A2 | 1/2006 |
| WO | WO 2006/017295 A2 | 2/2006 |

OTHER PUBLICATIONS

Database Registry, Mar. 13, 2006, XP002402671, compounds 876623-04-0, 876623-02-8.
Sushil K. Sharma, "Development of Peptidomimetics Targeting IAPs", International Journal of Peptide Research and Therapeutics, 12(1)2006(21-32).
Uma Screenivasan, "Synthesis and Dopamine Receptor Modulating Activity of Lactam Conformationally Constrained Analogues of Pro-Leu-Gly-NH2", Journal of Medicinal Chemistry, 1993, 36, 256-263.

*Primary Examiner* — Zinna Northington Davis

(57) ABSTRACT

The present disclosure relates to XIAP inhibitor compounds of the formula I.

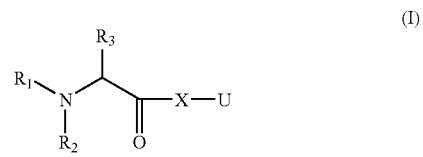

8 Claims, No Drawings

ORGANIC COMPOUNDS

This application is a U.S. National Phase filing of PCT/US2006/021850 filed Jun. 6, 2006, and claims priority to U.S. Provisional Application Serial No. 60/688,639 filed Jun. 8, 2005, the contents of which are incorporated herein by reference.

SUMMARY

The present invention relates generally to novel compounds that inhibit the binding of the Smac protein to Inhibitor of Apoptosis Proteins (IAPs). The present invention includes novel compounds, novel compositions, methods of their use and methods of their manufacture, wherein such compounds are generally pharmacologically useful as agents in therapies whose mechanism of action rely on the inhibition of the IAP/Caspase 9 or Smac/IAP interaction, and more particularly useful in therapies for the treatment of proliferative diseases, including cancer.

BACKGROUND

Programmed cell death plays a critical role in regulating cell number and in eliminating stressed or damaged cells from normal tissues. Indeed, the network of apoptotic signaling mechanisms inherent in most cell types provides a major barrier to the development and progression of human cancer. Since most commonly used radiation and chemotherapies rely on activation of apoptotic pathways to kill cancer cells, tumor cells which are capable of evading programmed cell death often become resistant to treatment.

Apoptosis signaling networks are classified as either extrinsic when mediated by death receptor-ligand interactions or intrinsic when mediated by cellular stress and mitochondrial permeabilization. Both pathways ultimately converge on individual Caspases. Once activated, Caspases cleave a number of cell death-related substrates, effecting destruction of the cell.

Tumor cells have devised a number of strategies to circumvent apoptosis. One recently reported molecular mechanism involves the over expression of members of the IAP family. IAPs sabotage apoptosis by directly interacting with and neutralizing Caspases. The prototype IAPs, XIAP and cIAP have three functional domains referred to as BIR 1, 2 & 3 domains. BIR3 domain interacts directly with Caspase 9 and inhibits its ability to bind and cleave its natural substrate, Procaspase 3.

It has been reported that a proapoptotic mitochondrial protein, Smac (also known as DIABLO), is capable of neutralizing XIAP and/or cIAP by binding to a peptide binding pocket (Smac binding site) on the surface of BIR3 thereby precluding interaction between XIAP and/or cIAP and Caspase 9. The present invention relates to therapeutic molecules that bind to the Smac binding pocket thereby promoting Caspase activation. Such therapeutic molecules are useful for the treatment of proliferative diseases, including cancer.

SUMMARY OF THE INVENTION

The present invention relates generally to novel compounds that mimic the binding of the Smac protein to Inhibitor of Apoptosis Proteins (IAPs). The present invention includes novel compounds, novel compositions, methods of their use and methods of their manufacture, where such compounds are generally pharmacologically useful as agents in therapies whose mechanism of action rely on the inhibition of the IAP/Caspase 9 or Smac/IAP interaction, and more particularly useful in therapies for the treatment of proliferative diseases, including cancer.

DETAILED DESCRIPTION

The present invention relates to compounds of the formula (I)

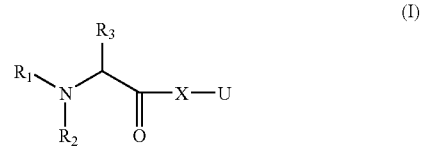

wherein
$R_1$ is H or $C_1$-$C_4$ alkyl;
$R_2$ is H, or $C_1$-$C_4$ alkyl which is unsubstituted or substituted by one or more substituents selected from halogen, —OH, —SH, —OCH$_3$, —SCH$_3$, —CN, —SCN and nitro;
$R_3$ is H, $C_1$-$C_4$ alkyl, —CF$_3$, —C$_2$F$_5$, —CH$_2$—Z or $R_2$ and $R_3$ together form with the nitrogen form a $C_3$-$C_6$heteroaliphatic ring;
Z is H, —OH, F, Cl, —CH$_3$; —CF$_3$, —CH$_2$Cl, —CH$_2$F or —CH$_2$OH;
X is a monocyclic or a bicyclic structure selected from the group consisting of:

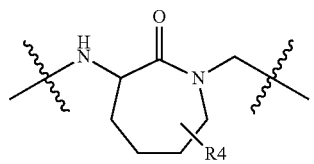

1

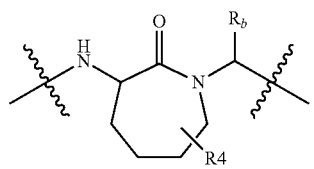

2

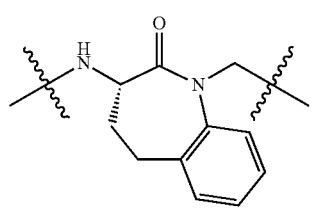

3

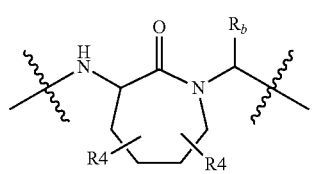

4

-continued
5
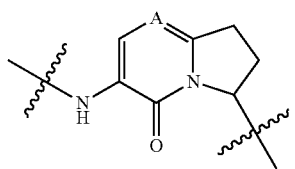
6
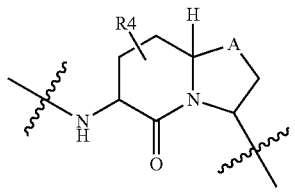
7
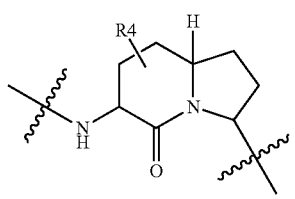
8
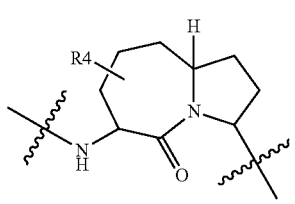
9
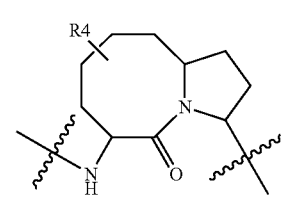
10
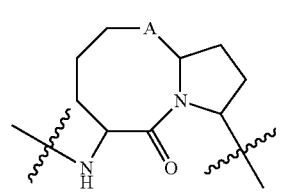
11
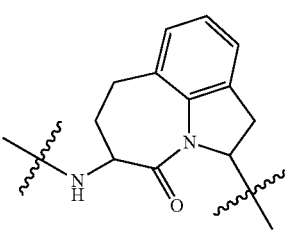
12
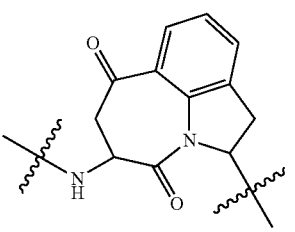
-continued
13
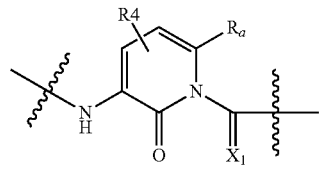
14
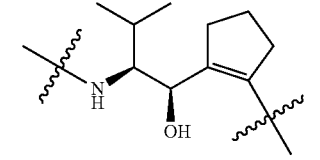
15
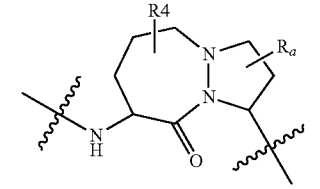
16
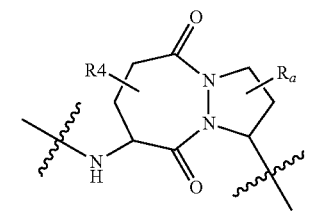
17
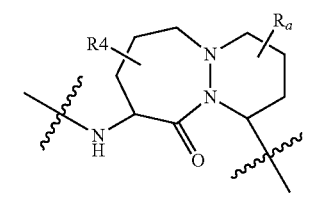
18
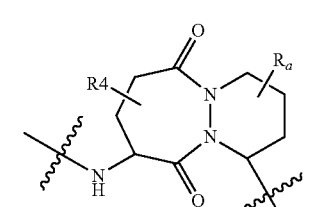
19
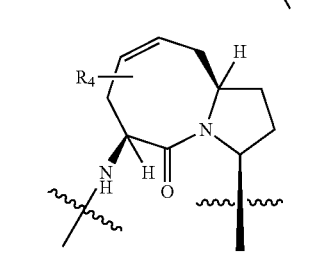
where
A is —CH$_2$, —CH—, N, O, or S;
X$_1$=O, S, or NR$_a$;
R$_4$, R$_a$ and R$_b$ are independently, H; C$_1$-C$_{16}$ straight or branched alkyl; C$_1$-C$_{16}$ alkenyl; C$_1$-C$_{16}$ alkynyl; or C$_1$-C$_{16}$ cycloalkyl; —(CH$_2$)$_{0-6}$-phenyl; (CH$_2$)$_{0-6}$-het; —O—C$_1$-C$_{16}$ straight or branched alkyl, —S—C$_1$-C$_{16}$ straight or branched alkyl; —N—C$_1$-C$_{16}$ straight or branched alkyl;

—O—$C_1$-$C_{16}$ alkenyl; —S—$C_1$-$C_{16}$ alkenyl; —N—$C_1$-$C_{16}$ alkenyl —O—$C_1$-$C_{16}$ cycloalkyl; —N—$C_1$-$C_{16}$ cycloalkyl; —S—$C_1$-$C_{16}$ cycloalkyl; —O—$(CH_2)_{0-6}$-phenyl; —N—$(CH_2)_{0-6}$-phenyl; —S—$(CH_2)_{0-6}$-phenyl; —O—$(CH_2)_{0-6}$-het; —N—$(CH_2)_{0-6}$-het and —S—$(CH_2)_{0-6}$-het wherein alkyl, cycloalkyl and phenyl are unsubstituted or substituted; or $R_4$ and $R_a$ may form a ring;

U is —$R_5$; —CH($R_5$)($R_6$); —CO—N($R_5$)($R_6$); —CO—O($R_5$); —CO—S($R_5$); —CS—N($R_5$)($R_6$); —N($R_5$)—CO—N($R_5$)($R_6$); —$C_1$-$C_5$-alkyl-N($R_5$)($R_6$); —$C_1$-$C_5$-alkyl-O($R_6$) or —$C_1$-$C_5$-alkyl-S(O)$_n$($R_6$) where n is 0, 1 or 2;

$R_5$ is H; $C_1$-$C_{10}$-alkyl; $C_3$-$C_7$-cycloalkyl; —$(CH_2)_{1-6}$—$C_3$-$C_7$cycloalkyl; —$C_1$-$C_{10}$alkyl-aryl; —$(CH_2)_{0-6}$-phenyl; —$(CH_2)_{0-6}$—$C_3$-$C_7$cycloalkyl-$(CH_2)_{0-6}$-phenyl; —$(CH_2)_{0-4}$CH—$((CH_2)_{1-4}$-phenyl)$_2$; —$(CH_2)_{0-6}$—CH(phenyl)$_2$; —C(O)—$C_1$-$C_{10}$alkyl; —C(O)—$(CH_2)_{1-6}$—$C_3$-$C_7$cycloalkyl; —C(O)—$(CH_2)_{0-6}$-phenyl; —$(CH_2)_{1-6}$-het; —C(O)—$(CH_2)_{1-6}$-het; —$(CR_7R_8)_{0-2}$-Aryl-V-Aryl; CHR$_6$C(O)N($R_{12}$)($R_{13}$); C(O)—NH—CH($R_{11}$)($R_{14}$) or $R_5$ is a residue of an amino acid, wherein the alkyl, cycloalkyl, phenyl and aryl substituents are unsubstituted or substituted;

or when U is —CO—N($R_5$)($R_6$); —CS—N($R_5$)($R_6$); —N($R_5$)—CO—N($R_5$)($R_6$); or N($R_5$)—CO—N($R_5$)($R_6$), $R_5$ and $R_6$ together with the N atom form an aromatic or aliphatic heterocycle;

$R_7$ and $R_8$ are independently H, halogen; $C_{1-7}$ alkyl; —OC$_{1-7}$ alkyl; $C_{1-7}$ cycloalkyl; or —OC$_{1-7}$ cycloalkyl wherein the alkyl, cycloalkyl substituents may be substituted or unsubstituted;

V is $R_9$; $R_{10}$; CR$_9$R$_{10}$; —C(O)—; C(hal)$_2$; —O—; —N(H)—; N(alkyl); N(aryl); S; SO; or S(O)$_2$;

$R_9$ and $R_{10}$ are independently H, halogen, $C_{1-7}$ alkyl; —OC$_{1-7}$ alkyl; $C_{1-7}$ cycloalkyl; or —OC$_{1-7}$ cycloalkyl wherein the alkyl, cycloalkyl substituents may be substituted or unsubstituted;

$R_6$ is H; —$C_1$-$C_{10}$ alkyl; —OH; —O—$C_1$-$C_{10}$-alkyl; —$(CH_2)_{0-6}$—$C_3$-$C_7$-cycloalkyl; —O—$(CH_2)_{0-6}$-aryl; —$(CH_2)_{0-6}$-aryl; phenyl; —$(CH_2)_{1-6}$-het; —O—$(CH_2)_{1-6}$-het; —N($R_{12}$)($R_{13}$); —CNOR$_{12}$; —S—$R_{12}$; —S(O)—$R_{12}$; —S(O)$_2$—$R_{12}$; or —S(O)$_2$—NR$_{12}$R$_{13}$ wherein the alkyl, cycloalkyl and aryl substituents are unsubstituted or substituted;

$R_{12}$ and $R_{13}$ are independently H; $C_1$-$C_{10}$ alkyl; —$(CH_2)_{0-6}$—$C_3$-$C_7$-cycloalkyl; —$(CH_2)_{0-6}$—(CH)$_{0-1}$(aryl)$_{1-2}$; —C(O)—$C_1$-$C_{10}$alkyl; —C(O)—$(CH_2)_{1-6}$—$C_3$-$C_7$-cycloalkyl; —C(O)—O—$(CH_2)_{0-6}$-aryl; —C(O)—$(CH_2)_{0-6}$—O-fluorenyl; —C(O)—NH—$(CH_2)_{0-6}$-aryl; —C(O)—$(CH_2)_{0-6}$-aryl; or —C(O)—$(CH_2)_{1-6}$-het, wherein the alkyl, cycloalkyl and aryl substituents are unsubstituted or substituted; or a substituent that facilitates transport of the molecule across a cell membrane, or $R_{12}$ and $R_{13}$ together with the nitrogen form an aromatic or aliphatic heterocycle;

where $R_{11}$ and $R_{14}$ are $C_{1-7}$ alkyl; —$(CH_2)_{0-6}$-phenyl; or amide;

aryl is phenyl, naphthyl, or indanyl which is unsubstituted or substituted; and wherein alkyl substituents may be substituted by one or more substituents selected from a double bond, halogen (hal), OH, SH, —O—$C_1$-$C_6$alkyl especially —OCH$_3$, —S—$C_1$-$C_6$ alkyl especially —SCH$_3$, —CN, —SCN, nitro, —N($R_1$)($R_2$) and —CF$_3$; alkyl as used in this application includes heteroalkyl wherein one of the carbon atoms in the alkyl chain is substituted with N, O or S;

cycloalkyl substituents may be substituted by one or more substituents selected from a double bond, $C_1$-$C_6$ alkyl, halogen, OH, SH, —O—$C_1$-$C_6$ alkyl especially —OCH$_3$, —S—$C_1$-$C_6$ alkyl especially —SCH$_3$, —CN, —SCN, nitro and —CF$_3$; and substituted phenyl or aryl are substituted by one or more substituents selected from halogen, hydroxy, $C_1$-$C_4$ alkyl, $C_1$-$C_4$ alkoxy, nitro, —CN, —O—C(O)—$C_1$-$C_4$ alkyl (substituted or unsubstituted) and —C(O)—O—$C_1$-$C_4$ alkyl (substituted or unsubstituted); and pharmaceutically acceptable salts thereof.

The present invention also relates to a method of treating a proliferative disease comprising administering a compound of the formula (I) to a warm-blooded animal, especially a human, and the use of a compound of the formula (I), especially for treating a proliferative disease. The present invention also relates to pharmaceutical preparations comprising a compound of the formula (I), especially for the treatment of a proliferative disease, a process for the manufacture of a compound of the formula (I), and novel starting materials and intermediates for their manufacture. The present invention also relates to the use of a compound of formula (I) in the manufacture of a pharmaceutical preparation for the treatment of a proliferative disease.

In a particularly important embodiment of the present invention, $R_3$ has the stereochemistry indicated in formula (II), with the definitions of the variable substituents and preferences described herein also applying to compounds having the stereochemistry indicated in formula (II).

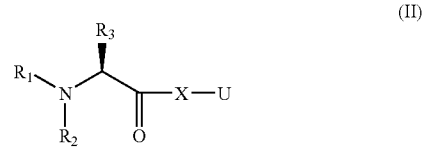

(II)

Preferred Embodiments

One embodiment of the present invention comprises a compound of formula (I):

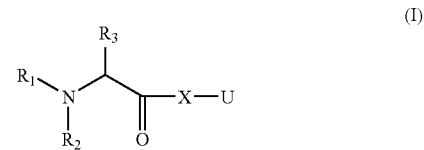

(I)

wherein
$R_1$ is H or $C_1$-$C_4$ alkyl;
$R_2$ is H or $C_1$-$C_4$ alkyl;
$R_3$ is H or $C_1$-$C_4$ alkyl;
X is a monocyclic or a bicyclic structure selected from the group consisting of:

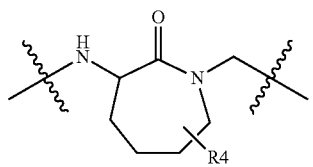

1

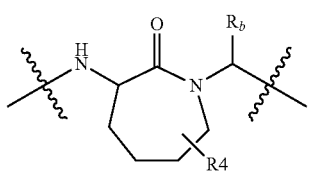
2
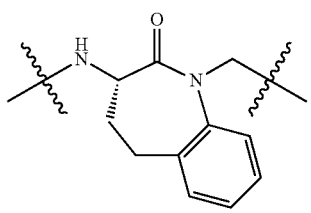
3
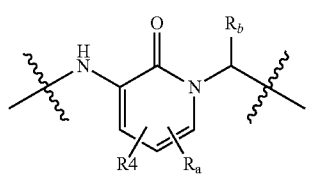
4
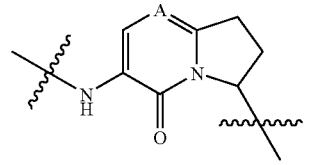
5
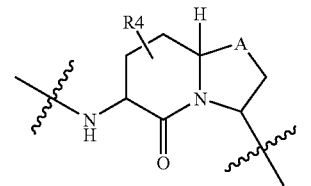
6
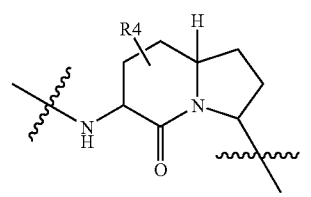
7
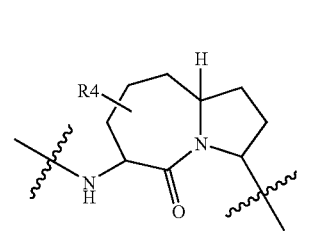
8
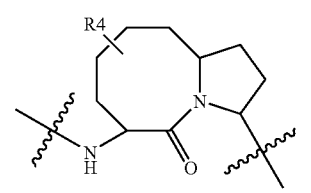
9
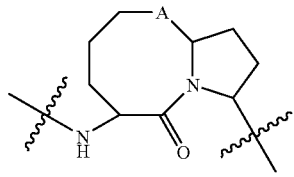
10
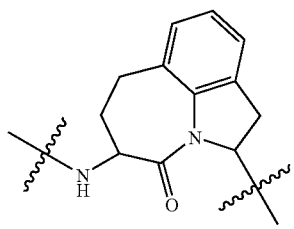
11
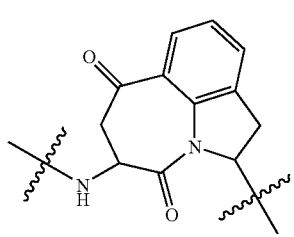
12
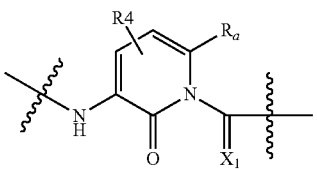
13
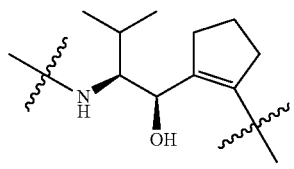
14
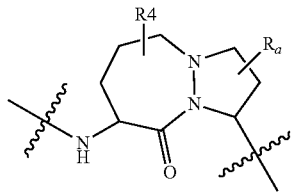
15
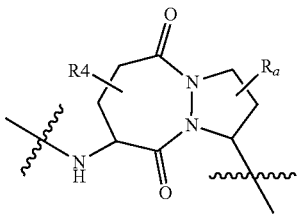
16
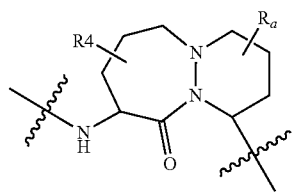
17

-continued

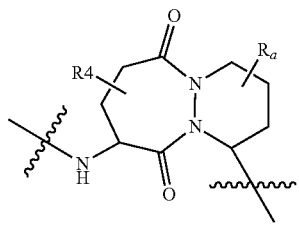
18

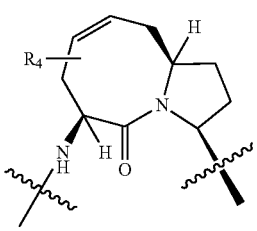
19 where
A is —CH$_2$, —CH—, N, O, or S;
X$_1$ is O, S, or NR$_a$;
R$_4$, R$_a$ and R$_b$ are independently, H; C$_1$-C$_{16}$ straight or branched alkyl or —(CH$_2$)$_{0-6}$-phenyl, wherein said phenyl may be unsubstituted or substituted, preferably with halo;
U is —R$_5$; —CH(R$_5$)(R$_6$); or —CO—N(R$_5$)(R$_6$);
R$_5$ is H; C$_1$-C$_{10}$-alkyl; —(CH$_2$)$_{0-6}$-phenyl; —C(O)—C$_1$-C$_{10}$alkyl; —C(O)—(CH$_2$)$_{0-6}$-phenyl; —(CR$_7$R$_8$)$_{0-2}$-Aryl-V-Aryl; CHR$_6$C(O)N(R$_{12}$)(R$_{13}$); or C(O)—NH—CH(R$_{11}$)(R$_{14}$);
R$_7$ and R$_8$ are independently H, halogen; C$_{1-7}$ alkyl; —OC$_{1-7}$ alkyl; C$_{1-7}$ cycloalkyl; or —OC$_{1-7}$ cycloalkyl;
V is —C(O)—; C(hal)$_2$; —O—; —N(H)—; N(alkyl); N(aryl); S; SO; or S(O)$_2$;
R$_9$ and R$_{10}$ are independently H, halogen, C$_{1-7}$ alkyl; —OC$_{1-7}$ alkyl; C$_{1-7}$ cycloalkyl; or —OC$_{1-7}$ cycloalkyl;
R$_6$ is H; —C$_1$-C$_{10}$ alkyl; —OH; —O—C$_1$-C$_{10}$-alkyl; —(CH$_2$)$_{0-6}$-phenyl; —(CH$_2$)$_{0-6}$-aryl; —O—(CH$_2$)$_{0-6}$-aryl; phenyl; —(CH$_2$)$_{1-6}$-het; —O—(CH$_2$)$_{1-6}$-het; —N(R$_{12}$)(R$_{13}$); —CNOR$_{12}$; —S—R$_{12}$; —S(O)—R$_{12}$; —S(O)$_2$—R$_{12}$; or —S(O)$_2$—NR$_{12}$R$_{13}$;
R$_{12}$ and R$_{13}$ are independently H; or C$_1$-C$_{10}$ alkyl;
where R$_{11}$ and R$_{14}$ are C$_{1-7}$ alkyl; —(CH$_2$)$_{0-6}$-phenyl; or amide;
aryl is phenyl, naphthyl, or indanyl which is unsubstituted or substituted;
and pharmaceutically acceptable salts thereof.

In an especially preferred embodiment is a compound of formula (I):

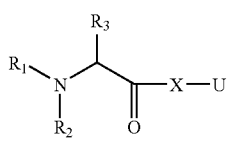
(I)

wherein
R$_1$, R$_2$ and R$_3$ are independently H or C$_1$-C$_4$ alkyl;
X is a monocyclic or a bicyclic structure selected from the group consisting of:

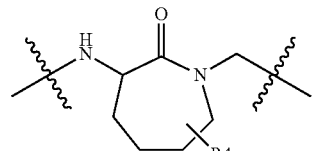
1

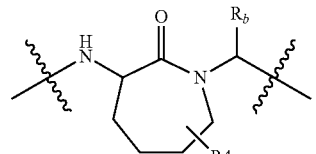
2

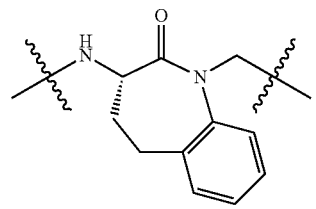
3

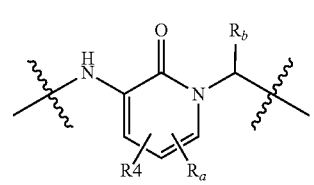
4

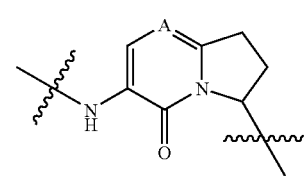
5

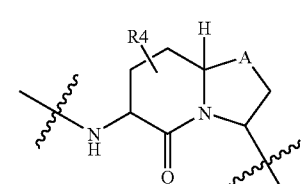
6

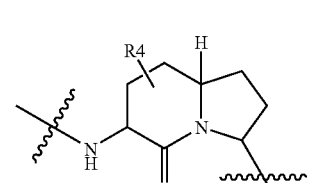
7

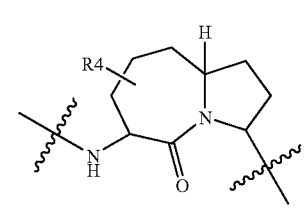
8

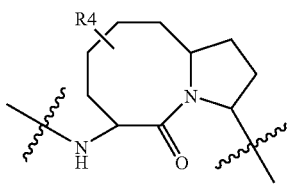
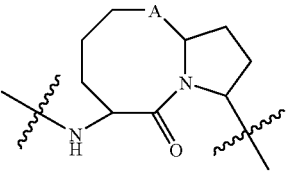
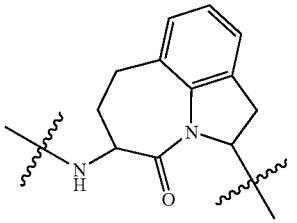
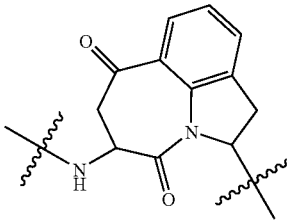
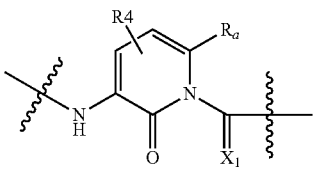
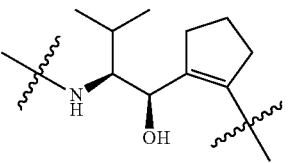
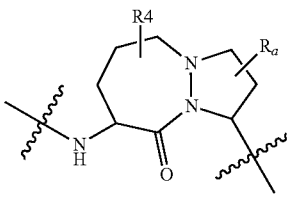
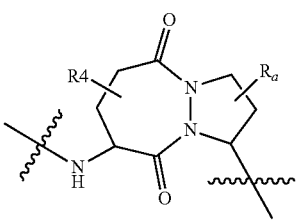
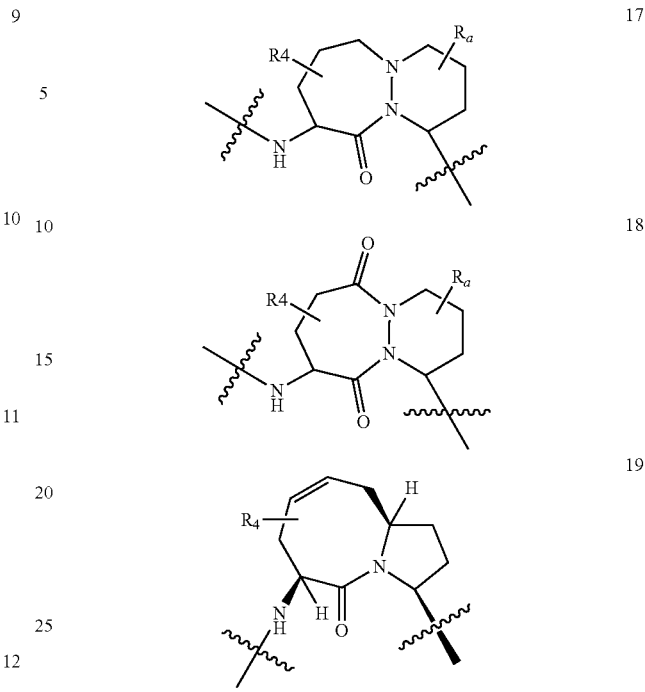

where
A is —CH$_2$—, —CH—, N, O, or S;
X$_1$ is O, S, or NR$_a$;
R$_4$, R$_a$ and R$_b$ are independently, H; C$_1$-C$_{16}$ straight or branched alkyl; or —(CH$_2$)$_{0-6}$-phenyl;
U is —R$_5$; C$_1$-C$_5$alkyl-N(R$_5$)(R$_6$); or —CO—N(R$_5$)(R$_6$);
R$_5$ is H; —(CH$_2$)$_{0-6}$-phenyl; C$_1$-C$_3$alkyl; -Aryl-V-Aryl-; or —C(O)—NH—CH(R$_{11}$)(R$_{14}$) wherein aryl or phenyl may be unsubstituted or substituted, preferably with halo;
V is —O—;
R$_6$ is H; —C$_1$-C$_{10}$ alkyl; —OH; —O—C$_1$-C$_{10}$-alkyl; —O—(CH$_2$)$_{0-6}$-phenyl; —(CH$_2$)$_{0-6}$-phenyl; indanyl; or phenyl;
where R$_{11}$ and R$_{14}$ are C$_{1-7}$ alkyl; —(CH$_2$)$_{0-6}$-phenyl; or amide;
aryl is phenyl, naphthyl, or indanyl which is unsubstituted or substituted;
and pharmaceutically acceptable salts thereof.

In other preferred embodiment of the present invention compound of formula (I) has the following:
R$_1$ is H or alkyl.
R$_2$ is especially H, methyl or ethyl, particularly H or methyl, which methyl group is unsubstituted or substituted, particularly unsubstituted methyl. R$_2$ as substituted methyl especially includes chloromethyl, dichloromethyl and especially trifluoromethyl.
R$_3$ is especially methyl or ethyl.
In a particular embodiment, R$_2$ and R$_3$ together with the nitrogen form a heteroaliphatic ring, including saturated and unsaturated 3 to 6 membered nonaromatic rings, for example, aziridine, azetidine, azole, piperidine, piperazine, and the like, especially aziridine and azetidine.
R$_4$ is preferably H, Me, n-Bu, benzyl, phenyl or phenyl-substituted halo.
R$_a$ is preferably H, Me, n-Bu, benzyl, phenyl or phenyl-substituted halo.
R$_b$ is preferably H.
R$_5$ is —(CH$_2$)$_{0-6}$—C$_3$-C$_7$-cycloalkyl-(CH$_2$)$_{0-6}$-phenyl includes fused cycloalkyl-phenyl rings, such as indanyl, when there are no methylenes between the cycloalkyl and phenyl rings.

$R_5$ as —$(CH_2)_{0-4}CH$—$((CH_2)_{1-4}$-phenyl)$_2$ is especially —$CH_2CH_2$-phenyl, indanyl;

$R_5$ as —$(CR_7R_8)_{0-2}$Aryl-V-Aryl is especially —$(CH_2)$-Ph-O-Ph or -Ph-O-Ph; Ph-C(O)-Ph; Ph-NH-Ph; Ph-N(Me)-Ph; Ph-S-Ph, Ph-SO$_2$-Ph; Ph-SO-Ph may be unsubstituted or substituted, preferably with halo.

$R_6$ is especially H.

A particularly important embodiment includes the compounds wherein $R_5$ is —$C_1$-$C_4$ alkyl-phenyl, especially those wherein $R_5$ is —$C_2H_4$-phenyl and $R_6$ is H.

In a particular embodiment of the present invention, one or both of $R_7$ and $R_8$ is H. If one of $R_7$ and $R_8$ is other than H, it is especially hydroxy, —$N(R_{12})(R_{13})$, especially wherein $R_{12}$ is —$C(O)$—$(CH_2)_{1-6}$—$C_3$-$C_7$-cycloalkyl, for example, wherein $(CH_2)_{1-6}$—$C_3$-$C_7$-cycloalkyl is cyclohexylmethyl, —$O$—$(CH_2)_{0-6}$-aryl, for example, wherein $(CH_2)_{0-6}$-aryl is benzyl. If only one of $R_7$ and $R_8$ is other than H, it is preferred for $R_8$ to be the substituent other than H.

In a preferred embodiment, $R_6$ is H and $R_5$ is —$C_1$-$C_{10}$ alkyl-aryl, particularly phenylmethyl, phenylethyl and phenylpropyl, indonyl especially phenylethyl and indanyl.

The general terms used hereinbefore and hereinafter preferably have, within this disclosure, the following meanings, unless otherwise indicated:

Unsubstituted is intended to mean that hydrogen is the only substituent.

Halogen is fluorine, chlorine, bromine or iodine, especially fluorine and chlorine. Unless otherwise specified alkyl substituents include straight or branched chain alkyl, such as methyl, ethyl, n-propyl, isopropyl, n-butyl, sec-butyl, tert-butyl, n-pentyl and branched pentyl, n-hexyl and branched hexyl, and the like.

Cycloalkyl substituents include cyclopropyl, cyclobutyl, cyclopentyl, cyclohexyl, and cycloheptyl.

The het substituents include aromatic and non-aromatic heterocyclic rings and fused rings containing aromatic and non-aromatic heterocyclic rings. Suitable het substituents include unsubstituted and substituted pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, 1,4-oxathiapane, furyl, thienyl, pyrrole, pyrazole, triazole, tetrazole, thiazole, oxazole, pyridine, pyrimidine, isoxazolyl, pyrazine, quinoline, isoquinoline, pyridopyrazine, pyrrolopyridine, furopyridine, indole, benzofuran, benzothiofuran, benzindole, benzoxazole, pyrroloquinoline, and the like. The het substituents are unsubstituted or substituted on a carbon atom by halogen, especially fluorine or chlorine, hydroxy, $C_1$-$C_4$ alkyl, such as methyl and ethyl, $C_1$-$C_4$ alkoxy, especially methoxy and ethoxy, nitro, —$O$—$C(O)$—$C_1$-$C_4$alkyl or —$C(O)$—$O$—$C_1$-$C_4$-alkyl or on a nitrogen by $C_1$-$C_4$ alkyl, especially methyl or ethyl, —$O$—$C(O)$—$C_1$-$C_4$ alkyl or —$C(O)$—$O$—$C_1$-$C_4$ alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazolyl, and the like.

Substituents that facilitate transport of the molecule across a cell membrane are known to those of skill in the medicinal chemistry arts (see, for example, Gangewar S., Pauletti G. M., Wang B., Siahaan T. J., Stella V. J., Borchardt R. T., *Drug Discovery Today*, vol. 2, p 148-155 (1997) and Bundgaard H. and Moss J., *Pharmaceutical Research*, vol. 7, p 885 (1990)). Generally, such substituents are lipophillic substituents. Such lipophillic substituents include a $C_6$-$C_{30}$ alkyl which is saturated, monounsaturated, polyunsaturated, including methylene-interrupted polyene, phenyl, phenyl which substituted by one or two $C_1$-$C_8$ alkyl groups, $C_5$-$C_9$ cycloalkyl, $C_5$-$C_9$ cycloalkyl which is substituted by one or two $C_1$-$C_8$ alkyl groups, —$X_1$-phenyl, —$X_1$-phenyl which is substituted in the phenyl ring by one or two $C_1$-$C_8$ alkyl groups, $X_1$-$C_5$-$C_9$ cycloalkyl or $X_1$-$C_5$-$C_9$ cycloalkyl which is substituted by one or two $C_1$-$C_8$ alkyl groups; where $X_1$ is $C_1$-$C_{24}$ alkyl which is saturated, monounsaturated or polyunsaturated and straight or branched chain.

It will be apparent to one of skill in the art when a compound of the invention can exist as a salt form, especially as an acid addition salt or a base addition salt. When a compound can exist in a salt form, such salt forms are included within the scope of the invention. Although any salt form may be useful in chemical manipulations, such as purification procedures, only pharmaceutically acceptable salts are useful for pharmaceutically products.

Pharmaceutically acceptable salts include, when appropriate, pharmaceutically acceptable base addition salts and acid addition salts, for example, metal salts, such as alkali and alkaline earth metal salts, ammonium salts, organic amine addition salts, and amino acid addition salts, and sulfonate salts. Acid addition salts include inorganic acid addition salts such as hydrochloride, sulfate and phosphate, and organic acid addition salts such as alkyl sulfonate, arylsulfonate, acetate, maleate, fumarate, tartrate, citrate and lactate. Examples of metal salts are alkali metal salts, such as lithium salt, sodium salt and potassium salt, alkaline earth metal salts such as magnesium salt and calcium salt, aluminum salt, and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

For the purposes of isolation or purification, as well as in the case of compounds that are used further as intermediates, it is also possible to use pharmaceutically unacceptable salts, e.g., the picrates. Only pharmaceutically acceptable, non-toxic salts may be used for therapeutic purposes, however, and those salts are therefore preferred.

Synthetic Procedure

Abbreviations $CH_2Cl_2$ methylene chloride
$CH_3CN$ acetonitrile
DIBAL diisobutylaluminum hydride
DIPEA diisopropylethylamine
DME ethylene glycol dimethyl ether
DMF N,N-dimethylformamide
DTBB 4,4'-di-tert-butylbiphenyl
EtOAc ethyl acetate
HBTU O-benzyltriazol-1-yl-N,N,N',N'-tetramethyluronium hexafluorophosphate
HOBt 1-hydroxhbenzotriazole
HPLC high performance liquid chromatography
KOTMS potassium trimethysilanoate.
MeOH methanol
$MgSO_4$ magnesium sulfate
$MnO_2$ manganese dioxide
$Na_2CO_3$ sodium carbonate
$NaHCO_3$ sodium bicarbonate
NaOH sodium hydroxide Tetrakis tetrakis(triphenylphosphine)palladium(0)
TFA trifluoroacetic acid
THF tetrahydrofuran The compounds of formula (I) may be prepared as depicted below in Scheme 1:

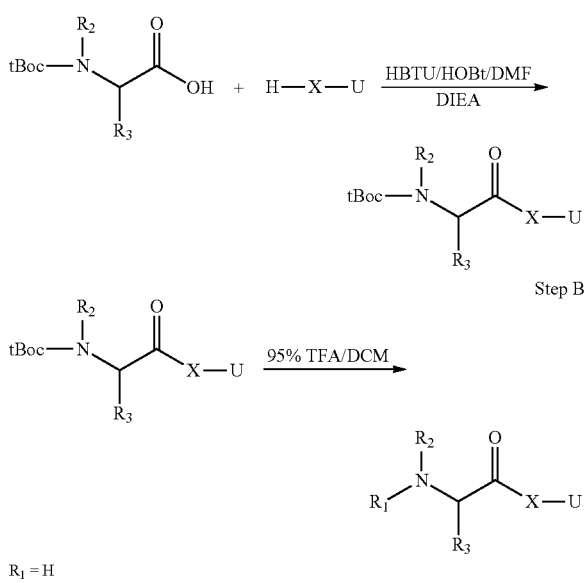

Step A: This step involves the coupling of an amine HXU (prepared in this invention or purchased from commercial sources) with a t-Boc-L-amino acid or its derivative using standard peptide coupling agents such as DCC/HOBt or HBTU/HOBt.

Step B: This step involves the removal of t-Boc group with trifluoroacetic acid (TFA).

As discussed above, the compounds of the present invention are useful for treating proliferative diseases. Thus, the present invention further relates to a method of treating a proliferative disease which comprises administering a therapeutically effective amount of a compound of the invention to a mammal, preferably a human, in need of such treatment.

A proliferative disease is mainly a tumor disease (or cancer) (and/or any metastases). The inventive compounds are particularly useful for treating a tumor which is a breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular, (i) a breast tumor; an epidermoid tumor, such as an epidermoid head and/or neck tumor or a mouth tumor; a lung tumor, for example, a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multi-drug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are implied alternatively or in addition, whatever the location of the tumor and/or metastasis.

The inventive compound is selectively toxic or more toxic to rapidly proliferating cells than to normal cells, particularly in human cancer cells, e.g., cancerous tumors, the compound has significant antiproliferative effects and promotes differentiation, e.g., cell cycle arrest and apoptosis.

The present invention further relates to a method of promoting apoptosis in rapidly proliferating cells, which comprises contacting the rapidly proliferating cells with an effective apoptosis promoting amount of a non-naturally-occurring compound that binds to the Smac binding site of XIAP and/or cIAP proteins. Preferably, the non-naturally-occurring compound a compound of present formula (I) or (II).

Pharmaceutical Compositions

The invention relates also to pharmaceutical compositions comprising a compound of formula (I), to their use in the therapeutic (in a broader aspect of the invention also prophylactic) treatment or a method of treatment of a kinase dependent disease, especially the preferred diseases mentioned above, to the compounds for said use and to pharmaceutical preparations and their manufacture, especially for said uses.

The present invention also relates to pro-drugs of a compound of formula (I) that convert in vivo to the compound of formula (I) as such. Any reference to a compound of formula (I) is therefore to be understood as referring also to the corresponding pro-drugs of the compound of formula (I), as appropriate and expedient.

The pharmacologically acceptable compounds of the present invention may be present in or employed, for example, for the preparation of pharmaceutical compositions that comprise an effective amount of a compound of the formula (I), or a pharmaceutically acceptable salt thereof, as active ingredient together or in admixture with one or more inorganic or organic, solid or liquid, pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g., lymphocytes), for the treatment of (this, in a broader aspect of the invention, also includes the prevention of (=prophylaxis against)) a disease that responds to inhibition of protein kinase activity, comprising an amount of a compound of formula (I) or a pharmaceutically acceptable salt thereof, preferably which is effective for said inhibition, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of a protein kinase and/or a proliferative disease, which comprises administering a (against the mentioned diseases) prophylactically or especially therapeutically effective amount of a compound of formula (I) according to the invention, or a tautomer thereof or a pharmaceutically acceptable salt thereof, especially to a warm-blooded animal, for example, a human, that, on account of one of the mentioned diseases, requires such treatment.

The dose of a compound of the formula (I) or a pharmaceutically acceptable salt thereof to be administered to warm-blooded animals, for example, humans of approximately 70 kg body weight, preferably is from approximately 3 mg to approximately 10 g, more preferably from approximately 10 mg to approximately 1.5 g, most preferably from about 100 mg to about 1,000 mg/person/day, divided preferably into 1-3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example, by means of conventional dissolving, lyophilizing, mixing, granulating or confectioning processes.

EXAMPLES

The following Examples serve to illustrate the invention without limiting the scope thereof.

The following examples are intended to illustrate, but not further limit, the invention.

Example 1

Synthesis of (1S,9S)-9-((S)-2-Methylamino-butyrylamino)-6,10-dioxo-octahydro-pyridazino[1,2-a][1,2]diazepine-1-carboxylic acid phenethyl-amide (1)

The title compound 1 (formula 1) is prepared according to the procedure set forth in Scheme 2.

Scheme 2

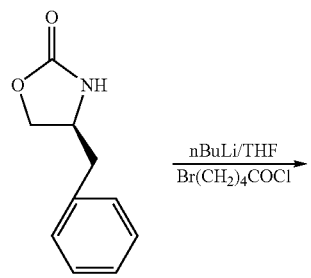

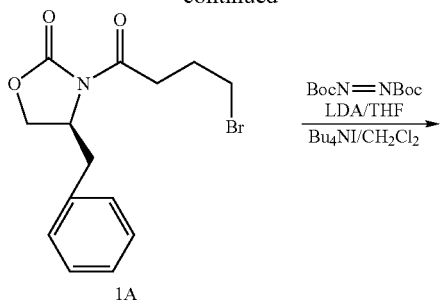

1A

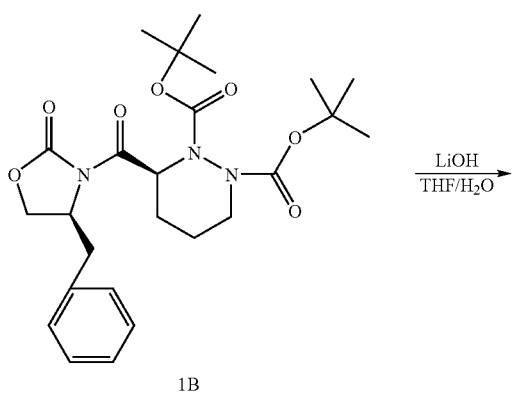

1B

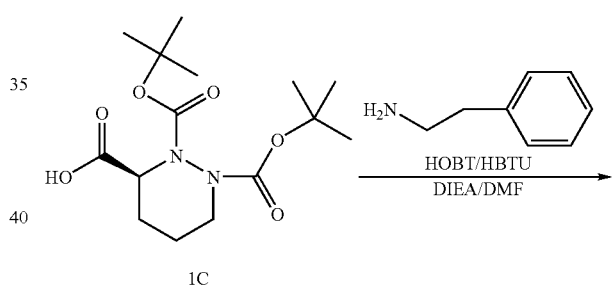

1C

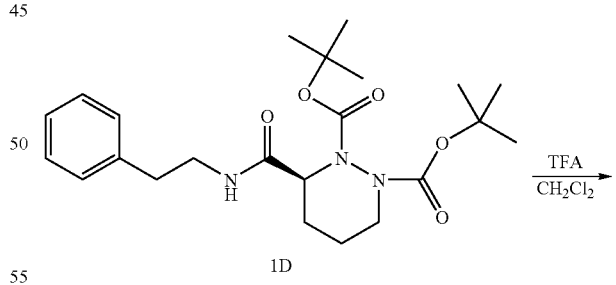

1D

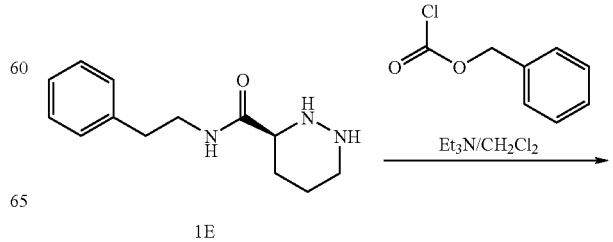

1E

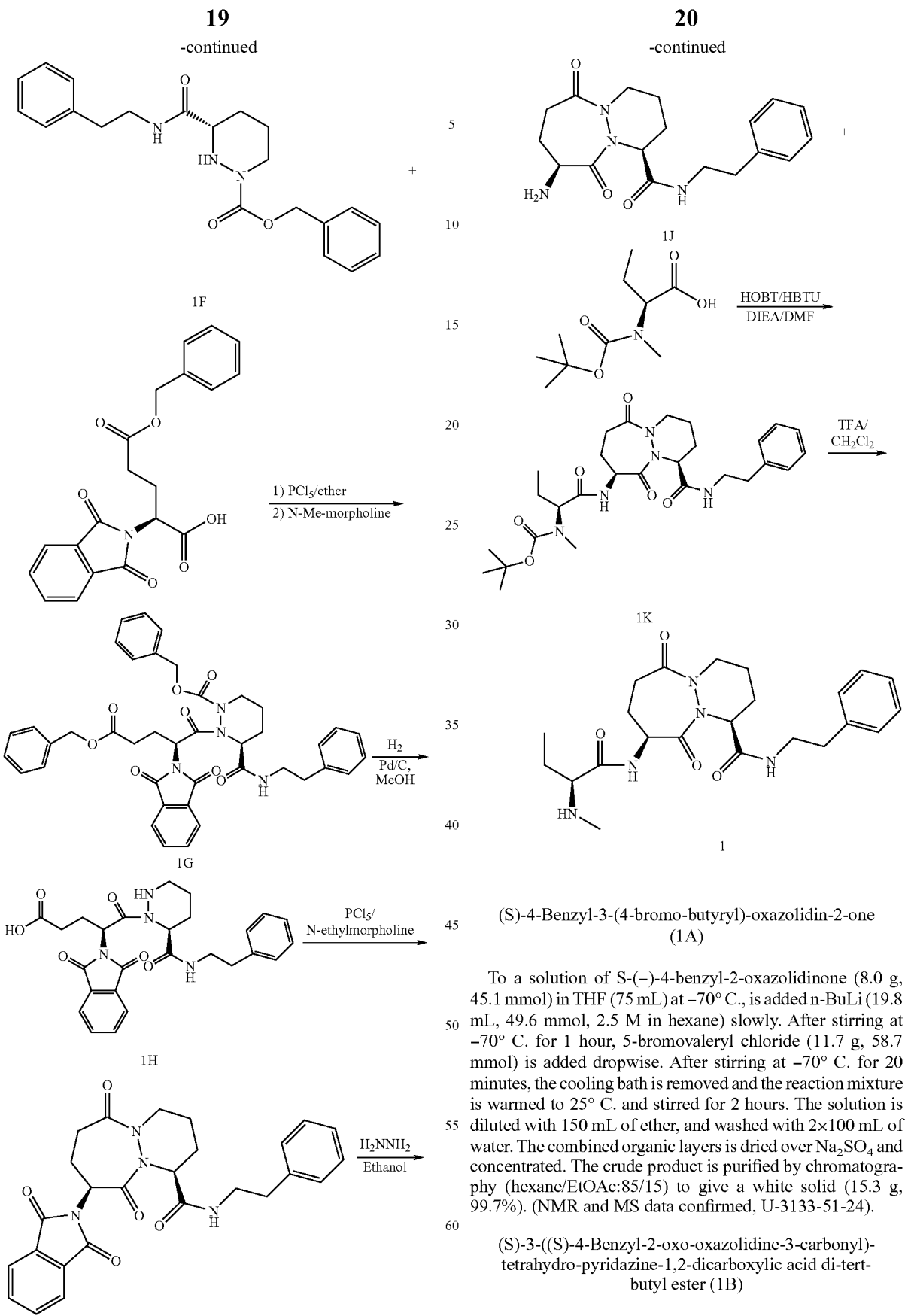

(S)-4-Benzyl-3-(4-bromo-butyryl)-oxazolidin-2-one (1A)

To a solution of S-(−)-4-benzyl-2-oxazolidinone (8.0 g, 45.1 mmol) in THF (75 mL) at −70° C., is added n-BuLi (19.8 mL, 49.6 mmol, 2.5 M in hexane) slowly. After stirring at −70° C. for 1 hour, 5-bromovaleryl chloride (11.7 g, 58.7 mmol) is added dropwise. After stirring at −70° C. for 20 minutes, the cooling bath is removed and the reaction mixture is warmed to 25° C. and stirred for 2 hours. The solution is diluted with 150 mL of ether, and washed with 2×100 mL of water. The combined organic layers is dried over $Na_2SO_4$ and concentrated. The crude product is purified by chromatography (hexane/EtOAc:85/15) to give a white solid (15.3 g, 99.7%). (NMR and MS data confirmed, U-3133-51-24).

(S)-3-((S)-4-Benzyl-2-oxo-oxazolidine-3-carbonyl)-tetrahydro-pyridazine-1,2-dicarboxylic acid di-tert-butyl ester (1B)

To a solution of diisopropylamine (0.77 mL, 5.53 mmol) in THF (4 mL) at 0° C. is added BuLi (2.17 mL, 5.42 mmol, 2.5 M in hexane) dropwise. The solution is stirred at 0° C. for 30 minutes to form an LDA solution. The LDA solution is cold to −70° C. and added to a solution of (S)-4-benzyl-3-(4-bromobutyryl)-oxazolidin-2-one (1.72 g, 5.07 mmol) in THF (4 mL) at −70° C. dropwise. After stirring at −70° C. for 2 hours, a solution of di-t-butyl azodicarboxylate (1.40 g, 6.08 mmol) in CH$_2$Cl$_2$ (4 mL) is added slowly. After stirring at −70° C. for 15 minutes, Bu$_4$NI (0.28 g, 0.76 mmol) is added in one portion. After stirring at −70° C. for 10 minutes, the flask with reaction mixture is moved to a −20° C. bath and stirred overnight (16 hours). The reaction mixture is quenched to ether (50 mL) with buffer solution (50 mL, Ph=7), and the mixture is extracted with ether (3×50 mL). The organic layer is dried over Na$_2$SO$_4$ and concentrated. The crude product is purified by chromatography (hexane/EtOAc:70/30) to give (S)-3-((S)-4-benzyl-2-oxo-oxazolidine-3-carbonyl)-tetrahydro-pyridazine-1,2-dicarboxylic acid di-tert-butyl ester as white solid (1.22 g, 49.3%). (NMR and MS data confirmed, U-3133-55-30).

(S)-Tetrahydro-pyridazine-1,2,3-tricarboxylic acid 1,2-di-tert-butyl ester (1C)

To a solution of (S)-3-((S)-4-benzyl-2-oxo-oxazolidine-3-carbonyl)-tetrahydro-pyridazine-1,2-dicarboxylic acid di-tert-butyl ester (1.22 g, 2.5 mmol) in THF (15 mL) at 0° C., is added a solution of LiOH (7 mL, 5% in H$_2$O). After stirring at 0° C. for 2 hours, the reaction mixture is diluted with 15 mL of water and extracted with 20 mL of ether. The ether layer is extracted with 10 mL of saturated NaHCO$_3$. The combined aqueous layers is acidified with saturated NaHSO$_4$ to Ph=2, and extracted with CH$_2$Cl$_2$ (3×20 mL). The combined organic layers is dried over Na$_2$SO$_4$ and concentrated to give clued product (0.83 g) as a pale gum without further purification for next step reaction. (NMR and MS data confirmed, U-3133-56-22).

(S)-3-Phenethylcarbamoyl-tetrahydro-pyridazine-1,2-dicarboxylic acid di-tert-butyl ester (1D)

To a solution of (S)-tetrahydro-pyridazine-1,2,3-tricarboxylic acid 1,2-di-tert-butyl ester (83 mg, 2.5 mmol) in DMF (10 mL) at room temperature, is added diisopropylethylamine (1.4 mL) slowly. After stirring at room temperature for 20 minutes, to the reaction mixture, is added phenethylamine (445 mg, 3.67 mmol), and followed by a solution of HOBT (545 mg, 4.04 mmol) and HBTU (1.53 g, 4.04 mmol) in DMF (10 mL). After stirring for 1.5 hours at room temperature, the reaction solution is diluted with ether (100 mL), and washed with water (2×50 mL). The combined organic solution is concentrated. The crude product is diluted with CH$_2$Cl$_2$ and dried over Na$_2$SO$_4$, and purified by chromatography (CH$_2$Cl$_2$/MeOH:97/3) to give (S)-3-phenethyl carbamoyl-tetrahydro-pyridazine-1,2-dicarboxylic acid di-tert-butyl ester as pale gum (920 mg, 83.6% in two steps). (NMR and MS data confirmed, U-3133-57-26).

(S)-Hexahydro-pyridazine-3-carboxylic acid phenethyl-amide (1E)

To a solution of (S)-3-phenethyl carbamoyl-tetrahydro-pyridazine-1,2-dicarboxylic acid di-tert-butyl ester (920 mg, 2.12 mmol) in CH$_2$Cl$_2$ (2 mL) at −20° C. is added TFA (4 mL, pre-cooled to −20° C.) slowly. After stirring at 0° C. for 30 minutes, the reaction mixture is concentrated by rotavaporation under room temperature. The residue is diluted with CH$_2$Cl$_2$/H$_2$O (20 mL, 8/2), and neutralized with 10% NH$_4$OH to Ph=7. After dried and concentrated to give crude (S)-hexahydropyridazine-3-carboxylic acid phenethylamide (376 mg, 76.4%) as pale gum without further purification for next step reaction. (NMR and MS data confirmed, U-3133-58-18).

(S)-3-Phenethylcarbamoyl-tetrahydro-pyridazine-1-carboxylic acid benzyl ester (1F)

To a solution of (S)-hexahydro pyridazine-3-carboxylic acid phenethyl-amide (376 mg, 1.59 mmol) and Et$_3$N (0.66 mL) in CH$_2$Cl$_2$ (10 mL) at 0° C., is added benzylchloroformate (270 mg, 1.59 mmol) dropwise. After stirring at −5° C. for 1.5 hours, the reaction mixture is diluted with CH$_2$Cl$_2$ (50 mL) and washed with 10 mL of water. The organic layer is dried over Na$_2$SO$_4$ and concentrated to give (S)-3-phenethylcarbamoyl-tetrahydro-pyridazine-1-carboxylic acid benzyl ester (580 mg) as pale gum without further purification for next step reaction. (NMR and MS data confirmed, U-3133-59).

(S)-2-[(S)-4-Benzyloxycarbonyl-2-(1,3-dioxo-1,3-dihydro-isoindol-2-yl)-butyryl]-3-phenethylcarbamoyl-tetrahydro-pyridazine-1-carboxylic acid benzyl ester (1G)

To a solution of (S)-2-(1,3-dioxo-1,3-dihydro-isoindol-2-yl)-pentanedioic acid 5-benzyl ester (580 mg, 1.59 mmol) in ether (25 mL) at 0° C., is added PCl$_5$ (920 mg, 4.38 mmol) in one portion. After stirring at 25° C. for 40 minutes, ether is removed by evaporation, and the residue is dissolved in 20 mL of THF, and is added to a solution of (S)-3-phenethylcarbamoyl-tetrahydro-pyridazine-1-carboxylic acid benzyl ester (580 mg) and N-methylmorpholine (0.74 mL, 6.77 mmol) in THF (10 mL) at 0° C. slowly. After stirring at room temperature for 2 hours, the reaction mixture is diluted with 100 mL of ether and washed with 2×20 mL of water. The combined organic layers is dried over Na$_2$SO$_4$ and concentrated, and purified by chromatography (CH$_2$Cl$_2$/MeOH:97/3) to give (S)-2-[(S)-4-benzyloxycarbonyl-2-(1,3-dioxo-1,3-dihydro-isoindol-2-yl)-butyryl]-3-phenethylcarbamoyl-tetrahydro-pyridazine-1-carboxylic acid benzyl ester (1.13 g, 99.2%) as pale solid. (NMR and MS data confirmed, U-3133-62).

(S)-4-(1,3-Dioxo-1,3-dihydro-isoindol-2-yl)-5-oxo-5-((S)-6-phenethylcarbamoyl-tetrahydro-pyridazin-1-yl)-pentanoic acid (1H)

A solution/suspension of (S)-2-[(S)-4-benzyloxycarbonyl-2-(1,3-dioxo-1,3-dihydro-isoindol-2-yl)-butyryl]-3-phenethylcarbamoyl-tetrahydro-pyridazine-1-carboxylic acid benzyl ester (1.13 g) and Pd/C (350 mg, 10% on carbon) in MeOH (15 mL, with 2 drops of acetic acid) in a 1,000 mL round flask is vigorously stirred at room temperature, under hydrogen gas (at atmosphere pressure) from a balloon for 3 hours. After degassed by house vacuum for 10 minutes, the reaction mixture is filtered to remove catalyst and concentrated. The crude product is diluted with CH$_2$Cl$_2$/H$_2$O (10 mL, 8/2) and neutralized with 10% NH$_4$OH to Ph=7. After dried and concentrated, the crude product is purified by chromatography (CH$_2$Cl$_2$/MeOH:97/3) to give (S)-4-(1,3-dioxo-1,3-dihydro-isoindol-2-yl)-5-oxo-5-((S)-6-phenethylcarbamoyl-tetrahydro-pyridazin-1-yl)-pentanoic acid (0.74 g, 95.3%) as pale solid. (NMR and MS data confirmed, U-3133-63).

(1S,9S)-9-(1,3-Dioxo-1,3-dihydro-isoindol-2-yl)-6,10-dioxo-octahydro-pyridazino[1,2-a][1,2]diazepine-1-carboxylic acid phenethyl-amide (1I)

To a solution of (S)-4-(1,3-dioxo-1,3-dihydro-isoindol-2-yl)-5-oxo-5-((S)-6-phenethylcarbamoyl-tetrahydro-pyridazin-1-yl)-pentanoic acid (0.74 g, 1.5 mmol) and N-methylmorpholine (0.6 g, 6.0 mmol) in THF (20 mL) at 0° C., is added PCl₅ (470 mg, 2.25 mmol) in one portion. After stirring at 0° C. for 3 hours, the reaction mixture is concentrated and purified by chromatography (CH₂Cl₂/MeOH:97/3) to yield (1S,9S)-9-(1,3-dioxo-1,3-dihydro-isoindol-2-yl)-6,10-dioxo-octahydro-pyridazino[1,2-a][1,2]diazepine-1-carboxylic acid phenethyl-amide (310 mg, 43.6%) as white solid. (NMR and MS data confirmed, U-3133-65).

(1S,9S)-9-Amino-6,10-dioxo-octahydro-pyridazino[1,2-a][1,2]diazepine-1-carboxylic acid phenethyl-amide (1J)

To a mixture/suspension of (1S,9S)-9-(1,3-dioxo-1,3-dihydro-isoindol-2-yl)-6,10-dioxo-octahydro-pyridazino[1,2-a][1,2]diazepine-1-carboxylic acid phenethyl-amide (310 mg, 0.70 mmol) and hydrozinehydrate (70 mg, 1.40 mmol) in ethanol (10 mL) is stirred at 60° C. for 2 hours. After cooled to room temperature and concentrated, the reaction mixture is purified by chromatography (CH₂Cl₂/MeOH:97/3) to give (1S,9S)-9-amino-6,10-dioxo-octahydro-pyridazino[1,2-a][1,2]diazepine-1-carboxylic acid phenethyl-amide (240 mg, 99%) as white solid. (NMR and MS data confirmed, U-3133-67).

[(S)-1-((4S,7S)-6,10-Dioxo-4-phenethylcarbamoyl-octahydro-pyridazino[1,2-a][1,2]diazepin-7-ylcarbamoyl)-propyl]-methyl-carbamic acid tert-butyl ester (1K)

To a solution of (S)-2-(tert-butoxycarbonyl-methylamino)-butyric acid (167 mg, 0.77 mmol) in DMF (5 mL) at room temperature, is added diisopropylethylamine (0.48 mL) slowly. After stirring at room temperature for 20 minutes, the solution is transferred to another flask contained (1S,9S)-9-amino-6,10-dioxo-octahydro-pyridazino[1,2-a][1,2]diazepine-1-carboxylic acid phenethyl-amide (240 mg, 0.70 mmol), and then a solution of HOBT (125 mg, 0.92 mmol) and HBTU (350 mg, 0.92 mmol) in DMF (5 mL) is added to the reaction mixture. After stirring for 1.5 hours, the reaction solution is diluted with ether (20 mL), and washed with water (2×10 mL). The combined organic layers is concentrated. The crude product is diluted with CH₂Cl₂ (10 mL) and dried over Na₂SO₄, and purified by chromatography (CH₂Cl₂/MeOH: 97/3) to give (S)-1-((4S,7S)-6,10-dioxo-4-phenethylcarbamoyl-octahydro-pyridazino[1,2-a][1,2]diazepin-7-ylcarbamoyl)-propyl]-methyl-carbamic acid tert-butyl ester (270 mg, 71.3%) as pale solid. (NMR and MS data confirmed, U-3133-69).

(1S,9S)-9-((S)-2-Methylamino-butyrylamino)-6,10-dioxo-octahydro-pyridazino[1,2-a][1,2]diazepine-1-carboxylic acid phenethyl-amide (1)

To a solution of (S)-1-((4S,7S)-6,10-dioxo-4-phenethylcarbamoyl-octahydro-pyridazino[1,2-a][1,2]diazepin-7-ylcarbamoyl)-propyl]-methyl-carbamic acid tert-butyl ester (270 mg, 0.50 mmol) in CH₂Cl₂ (1 mL) at −20° C. is added TFA (5 mL, pre-cooled to −20° C.) slowly. After stirring at 0° C. for 30 minutes, the reaction mixture is concentrated and purified by prep HPLC (column: waters prep C18 40×300 mm; mobile phase: gradient condition, started at CH₃CN 10%/H₂O 90% with 0.1% TFA, 10 minutes changed lineally to CH₃CN 100% with 0.1% TFA; flow rate: 25 mL/min.) to give (1S,9S)-9-((S)-2-methylamino-butyrylamino)-6,10-dioxo-octahydro-pyridazino[1,2-a][1,2]diazepine-1-carboxylic acid phenethyl-amide (230 mg) as TFA salt/white solid. (NMR and MS data confirmed, U-3133-73).

Example 2

Synthesis of (Z)-(2S,5S)-5-ethyl-1-[(S)-2-((S)-2-methylamino-propionylamino)-pentanoyl]-pyrrolidine-2-carboxylic acid phenethyl-amide (11) and (Z)-(3S,6S,10aR)-6-((S)-2-methylamino-propionylamino)-5-oxo-1,2,3,5,6,7,10,10a-octahydro-pyrrolo[1,2-a]azocine-3-carboxylic acid phenethylamide (12)

The title compounds 11 and 12 (formula 1) is prepared according to the procedure set forth in Scheme 3:

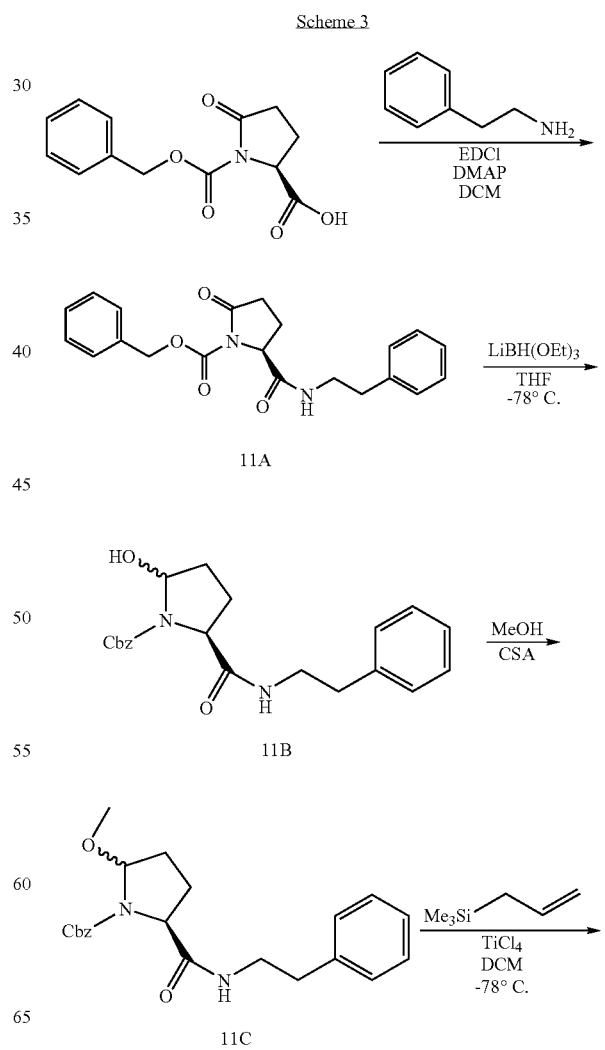

Scheme 3

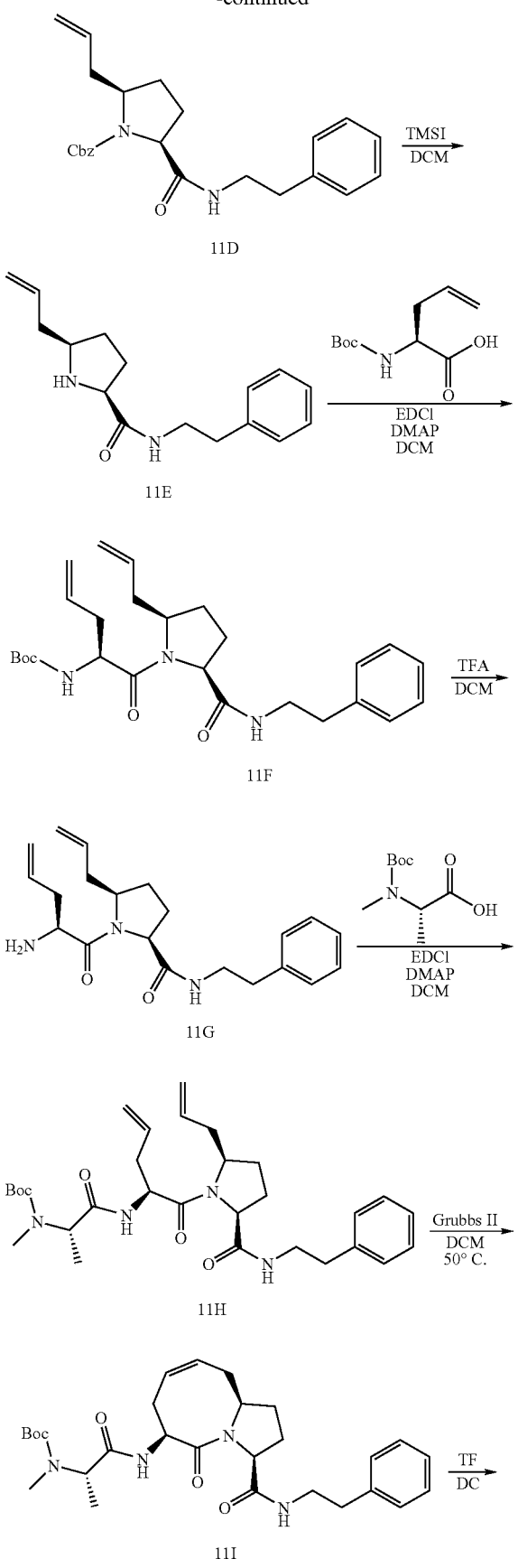
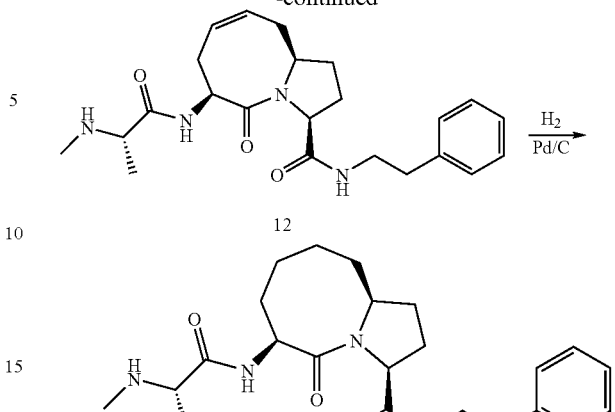

(S)-2-Oxo-5-phenethylcarbamoyl-pyrrolidine-1-carboxylic acid benzyl ester (11A)

(S)-5-Oxo-pyrrolidine-1,2-dicarboxylic acid 1-benzyl ester (14.9 g, 57 mmol) is suspended in dichloromethane (100 mL) and added DMAP (7.1 g, 58 mmol) while cooling on ice (0-5° C.). The suspension immediately clarified. EDCI (11.1 g, 58 mmol) is added resulting in precipitation which quickly clarified again. Phenethylamine (6.8 mL, 54 mmol) is added slowly via syringe. The reaction is complete in one half hour. The dichloromethane layer is washed with aqueous 10% citric acid, water and saturated bicarb, then dried over anhydrous sodium sulfate, filtered and concentrated to a white solid. LCMS characterization ES+367.1 (m+1).

(S)-5-Hydroxy-1-methyl-pyrrolidine-2-carboxylic acid phenethyl-amide (11B)

A THF solution of 11A pyroglutamide (3.9 g, 11 mmol) is chilled to −78° C. After 15 minutes, 1 M super-hydride solution (13 mL, 13 mmol) is slowly added. After 1 hour, it is carefully quenched with saturated bicarb and added 4 mL 30% hydrogen peroxide and concentrated to half volume and reconstituted with ethyl acetate, then washed with saturated bicarb and brine and dried over anhydrous sodium sulfate, filtered and concentrated to a clear oil. LCMS characterization ES+369.1 (m+1).

(S)-5-Methoxy-1-methyl-pyrrolidine-2-carboxylic acid phenethyl-amide (11C)

Product 11B is dissolved hemi-aminal in 10 mL anhydrous methanol and 100 mg 10-camphorsulfonic acid is added. Methanolysis is complete in 1 hour. The resulting material is filtered and concentrated, then reconstituted with ethyl acetate and washed with saturated bicarb followed by drying over anhydrous sodium sulfate, filtered and concentrated. LCMS characterization ES+383.1 (m+1).

(2S,5R)-5-Allyl-1-methyl-pyrrolidine-2-carboxylic acid phenethyl-amide (11D)

A dichloromethane (20 mL) solution of 11C methylaminal (7.7 g, 20 mmol) is chilled to −78° C. After 20 minutes, allyltrimethylsilane (6.5 mL, 40 mmol) is added. After 10 more minutes 1 M titanium(IV) chloride (24 mL, 24 mmol) is added slowly by syringe. The reaction is complete after 1 hour. The resulting material is carefully quenched (frothing) with saturated bicarb and extracted with dichlormethane, then washed with brine, dried over anhydrous magnesium sulfate, filtered and concentrated. The product is isolated by flash chromatography (SiO$_2$), and it crystallizes upon standing. LCMS characterization ES+393.1 (m+1).

(2S,5R)-5-Allyl-pyrrolidine-2-carboxylic acid phenethyl-amide (11E)

Dissolved 11D Cbz-homoallylproline amide (4.3 g, 11 mmol) in dichloromethane (11 mL, 1 M) is chilled to 0° C. Iodotrimethylsilane (5 mL, 37 mmol) is added via syringe. After complete reaction, it is diluted with diethyl ether and washed with 1 N HCl. Then it is concentrated aqueous with methanol titration to yield HCl salt of product. LCMS characterization ES+259.1 (m+1).

(2S,5R)-5-Allyl-1-((S)-2-methylamino-pent-4-enoyl)-pyrrolidine-2-carboxylic acid phenethyl-amide (11F)

AllylGlyOH (10.5 g, 26.4 mmol) is suspended in dichloromethane (200 mL) and EDCI (5.1 g, 26.4 mmol) and DMAP (3.2 g, 26.4 mmol) are added to obtain a clear solution. 11E homoallylproline amide in dichloromethane (50 mL) is added and stirred overnight. The product is quenched with saturated bicarb and extracted with dichloromethane, followed by washing with brine, drying over anhydrous magnesium sulfate, filtering and concentrating. The crude is used in following deprotection. LCMS characterization ES+456.1 (m+1).

(2S,5R)-5-Allyl-1-((S)-2-amino-pent-4-enoyl)-pyrrolidine-2-carboxylic acid phenethyl-amide (11G)

Product 11F is reconstituted in dichloromethane (40 mL) and added trifluoroacetic acid (10 mL). Stirring until reaction complete by HPLC. Toluene is added and concentrated to an amber oil. The product is dissolved in dichloromethane and washed with saturated bicarb followed by drying over anhydrous magnesium sulfate, filtering and concentrating to an amber solid. LCMS characterization ES+356.1 (m+1).

(2S,5R)-5-Allyl-1-[(S)-2-((S)-2-dimethylamino-propionylamino)-pent-4-enoyl]-pyrrolidine-2-carboxylic acid phenethyl-amide (11H)

Boc-N-MeAlaOH (5.36 g, 26.4 mmol) is suspended in dichloromethane (200 mL) and EDCI (5.4 g, 28 mmol) and DMAP (3.4 g, 28 mmol) are added to obtain a clear solution. 11G in dichloromethane (50 mL) is added and stirred overnight followed by quenching with saturated bicarb and extracting with dichloromethane then washing with brine, drying over anhydrous magnesium sulfate, filtering and concentrating. LCMS characterization ES+541.2 (m+1).

(Z)-(3S,6S,10aR)-6-((S)-2-Dimethylamino-propionylamino)-5-oxo-1,2,3,5,6,7,10,10a-octahydro-pyrrolo[1,2-a]azocine-3-carboxylic acid phenethyl-amide (11I)

Product 11G (894 mg) is dissolved in dichloromethane (50 mL) in a sealed tube under argon. Grubbs generation 2 catalyst (160 mg) is added and heated to 50° C., venting every half hour. After 6 hours, the product is concentrated and filtered through SiO$_2$ with 10% methanol in ethyl acetate. Concentrating and isolating product by HPLC purification. LCMS characterization ES+513.2 (m+1).

(Z)-(3S,6S,10aR)-6-((S)-2-Methylamino-propionylamino)-5-oxo-1,2,3,5,6,7,10,10a-octahydro-pyrrolo[1,2-a]azocine-3-carboxylic acid phenethyl-amide (12)

Product 11I is reconstituted in 20% trifluoroacetatic acid in dichloromethane (50 mL). Stirring until reaction complete by HPLC. Toluene is added and concentrated to an amber oil. The product is dissolved in dichloromethane and washed with saturated bicarb followed by drying over anhydrous magnesium sulfate, filtering and concentrating. HPLC purification to yield 12. LCMS characterization ES+413.1 (m+1).

(Z)-(2S,5S)-5-Ethyl-1-[(S)-2-((S)-2-methylamino-propionylamino)-pentanoyl]-pyrrolidine-2-carboxylic acid phenethyl-amide (11)

Product 12 bicyclic olefin (5 mg) is dissolved in ethyl acetate (2 mL) under N$_2$ atmosphere and added 10% palladium on carbon (20 mg). It is purged with H$_2$ and stirred vigorously for 1 hour followed by filtering and concentrating to obtain 11. LCMS characterization ES+415.1 (m+1).

Example 3

Synthesis of (S)-2-methylamino-N-[2-oxo-1-(phenethylcarbamoyl-methyl)-6-phenyl-1,2-dihydro-pyridin-3-yl]-propionamide (15)

The title compound 15 (formula 1) is prepared according to the procedure set forth in Scheme 4.

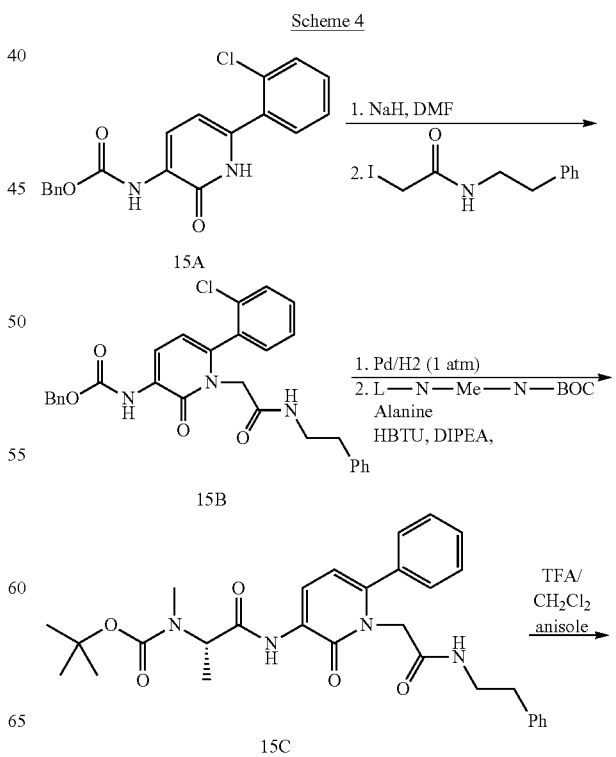

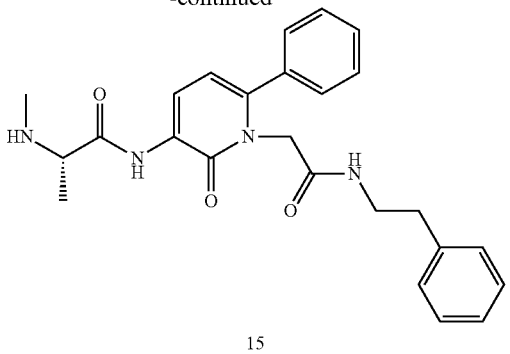

15

[6-(2-Chloro-phenyl)-2-oxo-1-(phenethylcarbamoyl-methyl)-1,2-dihydro-pyridin-3-yl]-carbamic acid benzyl ester (15B)

To a suspension of NaH (60% in mineral oil, 287 mg, 7.17 mmol, 1.2 eq.) in anhydrous DMF (12 mL) is added [6-(2-chloro-phenyl)-2-oxo-1,2-dihydro-pyridin-3-yl]-carbamic acid benzyl ester (15A) (Bernstein, P. R. et. al., J. Med. Chem., vol. 37, p 3313-3326 (1994)) (2.121 g, 5.98 mmol). After being stirred for 30 minutes, the orange solution is cooled to 0° C. and 2-iodo-N-phenethyl-acetamide (1.902 g, 6.58 mmol, 1.1 eq.) is added. The mixture is stirred at room temperature for 3 hours and is quenched with 1 N HCl (8 mL), extracted with ethyl acetate (3×). The organic layer is washed in sequence with 1 N HCl, saturated $Na_2S_2O_3$, water and brine; is dried over anhydrous $Na_2SO_4$ and concentrated. The residue is purified via silica gel chromatography (2-10% ethyl acetate in dichloromethane) to provide compound 15B as a yellow solid (605 mg, 20%):

$^1$H NMR (400 MHz, DMSO): δ 8.52 (bs, 1H), 7.96 (m, 1H), 7.93 (d, J=8H, 1H), 7.63-7.07 (m, 14H), 6.22 (d, J=8 Hz, 1H), 5.20 (bs, 2H), 4.89-3.75 (AB q, 2H), 3.20-3.11 (m, 2H), 2.57 (t, J=8 Hz, 2H); $^{13}$C NMR (100 MHz, MSO): δ 165.7, 157.0, 153.2, 139.1, 138.8, 136.4, 133.1, 132.6, 132.1, 131.4, 129.3, 128.5, 128.4, 128.3, 127.9, 129.8, 127.7, 127.5, 126.0, 121.0, 107.1, 66.1, 47.7, 40.2, 34.8; MS (ESI) m/e 516 (M+H$^+$), 395.

Methyl-{(S)-1-[(2-oxo-1-(phenethylcarbamoyl-methyl)-6-phenyl-1,2-dihydro-pyridin-3-ylcarbamoyl]-ethyl}-carbamic acid tert-butyl ester (15C)

To compound 15B (595 mg, 1.15 mmol) above in anhydrous ethanol (24 mL) is added sodium methoxide (65 mg, 1.21 mmol) and palladium on carbon (10%, 236 mg, 40%). The mixture is hydrolyzed under hydrogen (1 atm) for 4 days. The mixture is filtered and washed with methanol. The filtrate is concentrated and the resulting residue is dissolved in anhydrous DMF (2 mL) followed by treatment at 0° C. with a solution prepared below: To (S)—N-methyl-N—BOC-alanine (240 mg, 1.18 mmol, 1.05 eq.) in anhydrous acetonitrile (2 mL) is added Hunig base (390 μL, 2.24 mmol, 2 eq.) and HBTU (447 mg, 1.18 mmol, 1.05 eq.) at 0° C. and kept at temperature for 30 minutes. The whole reaction mixture is stirred at room temperature for 36 hours and 50° C. for 7 hours; and quenched with water and 1 N HCl (2 mL). The mixture is extracted with ethyl acetate (3×). The organic layer is washed with water and brine; dried over anhydrous $Na_2SO_4$. Upon concentration the residue is purified through silica gel chromatography (20-30% ethyl acetate in hexane) to provide compound 15C as a white solid (86 mg, 15%):

$^1$H NMR (400 MHz, CDCl$_3$): δ 8.70 (bs, 1H), 8.34 (d, J=8 Hz, 1H), 7.35-7.04 (m, 10H), 6.19 (bs, 1H), 6.13 (d, J=8H), 4.35 (AB q, 2H), 4.06 (q, J=4 Hz, 1H), 3.42 (m, 2H), 2.79 (bs, 3H), 2.71 (t, J=4 Hz, 2H), 1.36 (d, J=8 Hz, 3H); $^{13}$C NMR (100 MHz, CDCl$_3$): δ 170.7, 167.0, 158.1, 155.5, 142.8, 138.6, 134.5, 129.4, 129.3, 128.7, 128.6, 128.5, 127.8, 126.5, 122.3, 108.6, 80.9, 40.8, 35.5, 29.3, 28.3, 14.1, 13.7; MS (ESI) m/e 522 (M+H$^+$).

(S)-2-Methylamino-N-[2-oxo-1-(phenethylcarbamoyl-methyl)-6-phenyl-1,2-dihydro-pyridin-3-yl]-propionamide (15)

Compound 15C (74 mg, 0.14 mmol) from above is treated with anisole (45 μL, 0.42 mmol) and TFA (1 mL) in anhydrous dichloromethane (1 mL) for 4 hours. The mixture is concentrated and the residue is treated with dichloromethane (1 mL). The solution is added dropwise to a rapidly stirring mixture of hexane and anhydrous ether (10.5 mL). The resulting slurry is filtered, leaving a white solid that is washed with the same solvent mixture twice and dried in vacuo to afford compound 1 as a TFA salt (45 mg, 59%):

$^1$H NMR (400 MHz, DMSO): δ 10.08 (s, 1H), 8.83 (bs, 2H), 8.22 (d, J=8 Hz, 1H), 8.05 (t, J=4 Hz, 1H), 7.44-7.08 (m, 10H), 6.18 (d, J=8 Hz, 1H), 4.32 (s, 2H), 4.18 (q, J=4 Hz), 3.19 (m, 2H), 2.59 (t, J=8 Hz), 2.43 (bs, 3H), 1.39 (d, J=3 Hz, 3H); $^{13}$C NMR (100 MHz, DMSO): δ 168.5, 166.4, 157.6, 157.1, 144.1, 139.2, 134.7, 129.3, 128.7, 128.6, 128.5, 128.3, 126.6, 126.1, 124.1, 106.6, 56.7, 49.0, 35.0, 30.9, 16.0; MS (ESI) m/e 433 (M+H$^+$), 312.

Example 4

Synthesis of (S)—N-[6-phenyl-2-oxo-1-(3-phenoxy-benzyl)-1,2-dihydro-pyridin-3-yl]-2-methylamino-propionamide (20)

The title compound 20 (formula 1) is prepared according to the procedure set forth in Scheme 5:

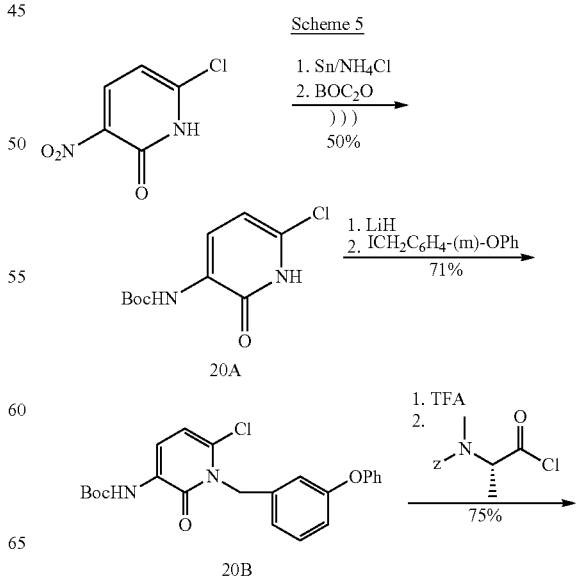

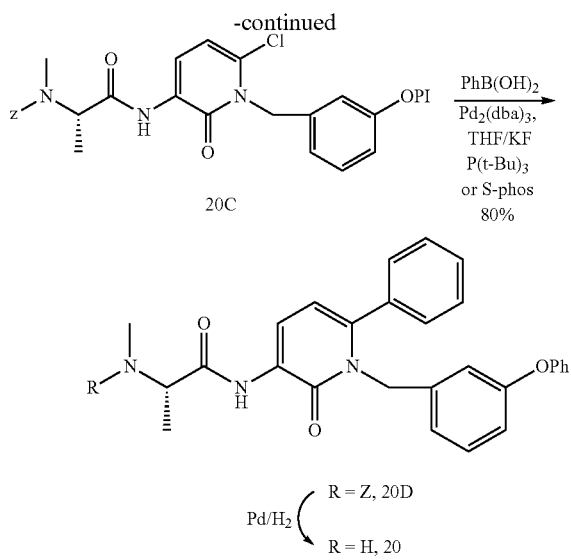

(6-Chloro-2-oxo-1,2-dihydro-pyridin-3-yl)-carbamic acid tert-butyl ester (20A)

A suspension of tin powder (2 g, 17.20 mmol, 2.5 eq.), ammonium chloride (2.576 g, 48.16 mmol, 7 eq.) and 6-chloro-3-nitro-1H-pyridien-2-one (1.201 g, 6.88 mmol, Moody, C. J. et al., J. Chem. Soc. Perkin Trans I, p 955 (2001)) in anhydrous methanol (14 mL) is sonicated for 3 hours. The solvent is removed from the mixture by rotary evaporation. The residue is treated with anhydrous THF (14 mL) and Boc anhydride (3.00 g, 13.76 mmol, 2 eq.) and the mixture is heated at reflux for 18 hours. More Boc anhydride (0.90 g, 0.6 mmol) is added to the mixture and reflux continued for 14 hours. The mixture is filtered through a silica gel pad with 2% methanol in methylene chloride washing. The filtrate is concentrated and the residue is purified by silica gel chromatography (0-2% methanol in methylene chloride) to afford the title compound 20A (1.12 g, 58.9%):

$^1$H NMR (400 MHz, CDCl$_3$): δ 7.95 (bd, J=8 Hz, 1H), 7.33 (bs, 1H), 71.45 (s, 9H); $^{13}$C NMR (100 MHz, CDCl$_3$): δ 158.9, 152.6, 127.8, 126.5, 122.6, 107.6, 81.2, 28.3; MS (ESI) m/e 245 (M+H$^+$), 191, 189 (U3910-65).

6-Chloro-2-oxo-1-(3-phenoxy-benzyl)-1,2-dihydropyridin-3-yl]-carbamic acid tert-butyl ester (20B)

To lithium hydride (53 mg, 6.67 mmol) in anhydrous DMF/DME (7.6/2.6 mL) is added at 0° C. pyridone 20A (1.255 g, 5.13 mmol). The mixture is stirred at room temperature for 30 minutes, then 3-phenoxy-benzyl iodide (1.43 mL, 7.19 mmol) is added and the mixture is heated at 75° C. for 3 hours. The reaction mixture is quenched with icy water and extracted with ethyl acetate (3×). The organic phase is washed with brine (5×), dried over anhydrous sodium sulfate. Upon filtration and concentration the residue showed the presence of ca. 80/20 of the N-/O-alkylation products by $^1$H NMR (the two structures were distinguished by HMBC). The crude product is purified by silica gel chromatography (2.5-5.0% ethyl acetate in hexane) to afford the desired pyridone 20B (1.544 g, 70.5%):

$^1$H NMR (400 MHz, CDCl$_3$): δ 7.88 (bs, d, J=8 Hz, 1H), 7.51 (bs, 1H), 71.28-6.81 (m, 9H), 6.28 (d, J=8 Hz, 1H); $^{13}$C NMR (100 MHz, CDCl$_3$): δ 158.1, 157.6, 156.9, 152.7, 137.6, 130.0, 129.8, 128.6, 127.7, 123.4, 121.9, 119.2, 117.9, 117.8, 107.3, 81.0, 49.5, 28.2; MS (ESI) m/e 427 (M+H+), 371 (U3910-76).

{(S)-1-[6-Chloro-2-oxo-1-(3-phenoxy-benzyl)-1,2-dihydro-pyridin-3-ylcarbamoyl]-ethyl}-methyl-carbamic acid benzyl ester (20C)

To compound 20B (410 mg, 0.836 mmol) in anhydrous methylene chloride (0.65 mL) is added anisole (0.31 mL) and TFA (2.0 mL). The mixture is stirred for 2 hours and is added dropwise to a rapidly stirring mixture of methylene chloride and anhydrous ether (15/1 mL). The top solution is decanted and the bottom oil is dried in vacuo. The greenish amine residue is dissolved in anhydrous methylene chloride (2.5 mL) with 2,4,6-trimethylpyridine (0.39 mL, 2.93 mmol).

In another flask is placed L-N-methyl Z-analine (536 mg, 2.26 mmol) and methylene chloride (2.5 mL). The mixture is treated at 0° C. with 1-chlorine-N,N,2-trimethylpropenylamine (0.30 mL, 2.26 mmol). The reaction mixture is stirred at 0° C. for 20 minutes and at the same temperature, is treated with the above mentioned amine solution. After being stirred at 0° C. for 2 hours and room temperature for 1 hour, the reaction mixture is concentrated. The residue is quenched with water and extracted with ethyl acetate (3×). The organic phase is washed with saturated citric acid, saturated sodium bicarbonate and brine (3×), dried over anhydrous sodium sulfate. Upon filtration, concentration and purification by silica gel chromatography (15-20% ethyl acetate in hexane) the desired compound 20C (363 mg, 75.0%) is obtained:

$^1$H NMR (400 MHz, CDCl$_3$): δ 8.84 (bs, 1H), 8.30 (bs, 1H), 7.35-6.86 (m, 14H), 6.36 (d, J=8 Hz, 1H), 5.46 (AB, 2H), 5.29 (br, 2H), 5.19-4.98 (b, 1H), 2.92 (bs, 3H), 1.43 (d, J=8 Hz, 3H); $^{13}$C NMR (100 MHz, CDCl$_3$): δ170.4, 158.2, 157.6, 156.8, 137.4, 136.3, 130.1, 129.8, 129.6, 128.5, 128.1, 127.7, 123.5, 122.0, 121.8, 119.1, 117.8, 107.2, 67.9, 55.8, 49.6, 30.0, 14.4; MS (ESI) m/e 546 (M+H$^+$) (U3910-80, 83 and 100).

{(S)-1-[6-Phenyl-2-oxo-1-(3-phenoxy-benzyl)-1,2-dihydro-pyridin-3-ylcarbamoyl]-ethyl}-methyl-carbamic acid benzyl ester (20D)

To a mixture of compound 20C (37 mg, 0.068 mmol), phenyl boronic acid (12 mg, 0.10 mmol) tri-tert-butylphosphonium tetra fluoroborate (16 mg, 0.054 mmol), tris(dibenzylideneacetone) dipalladium (12 mg, 0.027 mmol) and potassium fluoride (61 mg, 1.0 mmol) is added under nitrogen atmosphere anhydrous THF (1.0 mL). The mixture is heated at reflux for 20 hours and is concentrated. The residue is purified by silica gel preparative TLC (40% ethyl acetate in hexane) to provide the title compound 20D (32 mg, 80%):

$^1$H NMR (400 MHz, CDCl$_3$): δ 8.90 (bs, 1H), 8.32 (bs, 1H), 7.33-7.00 (m, 14H), 6.86 (m, 2H), 6.75 (dd, J=8, 8 Hz, 1H), 6.58 (m, 1H), 6.43 (bs, 1H), 6.10 (d, J=8 Hz, 1H), 5.18-4.75 (m, 5H), 2.88 (bs, 3H), 1.39 (d, J=8 Hz, 3H); $^{13}$C NMR (100 MHz, CDCl$_3$): δ 170.5, 158.0, 157.5, 156.8, 142.7, 138.7, 134.9, 129.9, 129.7, 129.2, 129.1, 128.5, 128.4, 128.1, 123.4, 122.0, 121.4, 119.1, 117.5, 117.0, 108.5, 64.8, 55.8, 49.2, 30.1, 13.8; MS (ESI) m/e 588 (M+H$^+$) (U3910-108).

(S)—N-[6-Phenyl-2-oxo-1-(3-phenoxy-benzyl)-1,2-dihydro-pyridin-3-yl]-2-methylamino-propionamide (20)

Compound 20D (55 mg, 0.094 mmol) in ethanol (2 mL) is hydrogenated under 10% palladium on carbon (10 mg) and hydrogen (balloon pressure). The reaction is monitored by LCMS. Upon completion the mixture is filtered and the filtrate is concentrated and purified by HPLC to afford the title compound (5 mg, 12%):

$^1$H NMR (400 MHz, CDCl$_3$): δ 8.96 (bs, 1H), 8.33 (d, J=8 Hz, 1H), 7.36-7.02 (m, 9H), 6.85 (d, J=8 Hz, 2H), 6.75 (dd, J=8, 8 Hz, 1H), 6.56 (d, J=8 Hz, 1H), 6.42 (bs, 1H), 6.17 (d, J=6, 1H), 5.12 (bs, 2H), 4.06 (bs, 1H), 2.70 (bs, 3H), 1.62 (d, J=4 Hz, 3H); MS (ESI) m/e 454 (M+H$^+$), (U3910-116).

Examples 1-30

The following compounds are prepared by methods analogs to those described herein utilizing analogous starting materials:

Table 1

| Compound Structure | Example Number |
|---|---|
| 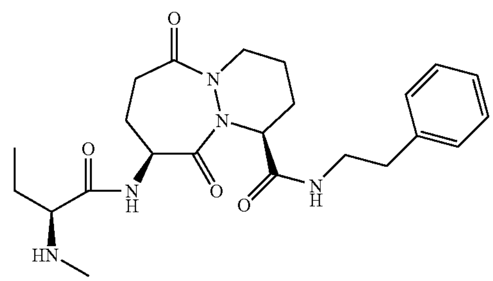 | Example 1<br>MS ESI 444.55<br>(M + H)$^+$ |
| 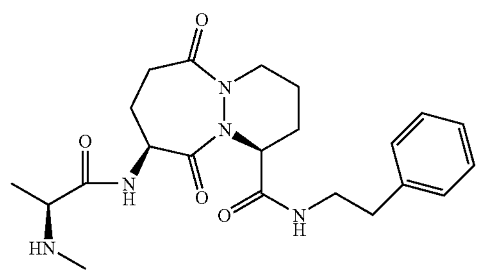 | Example 2<br>MS ESI 430.52<br>(M + H)$^+$ |
| 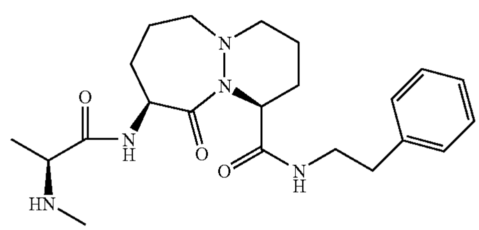 | Example 3<br>MS ESI 416.54<br>(M + H)$^+$ |
| 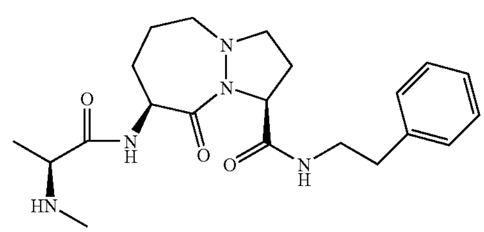 | Example 4<br>MS ESI 402.51<br>(M + H)$^+$ |
| 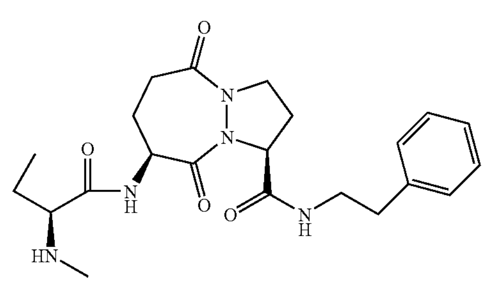 | Example 5<br>MS ESI 430.2<br>(M + H)$^+$ |

-continued

| Compound Structure | Example Number |
|---|---|
| 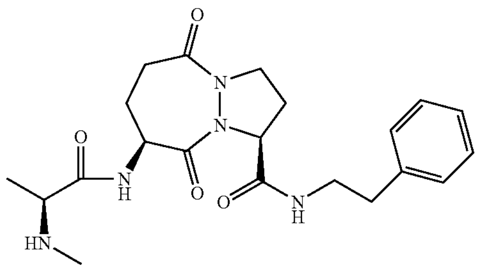 | Example 6<br>MS ESI 415.50<br>(M + H)+ |
| 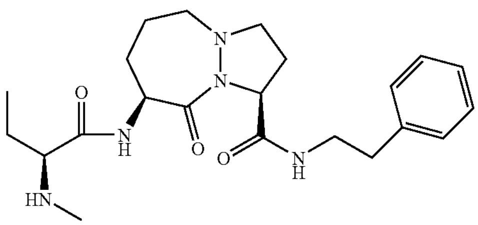 | Example 7<br>MS ESI 416.54<br>(M + H)+ |
| 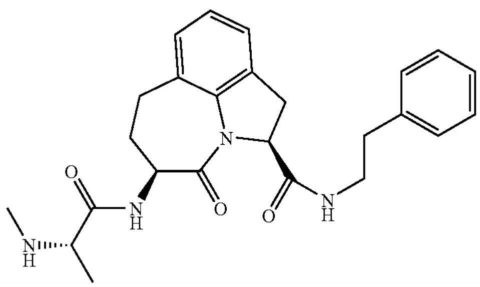 | Example 8<br>MS ESI 435.54<br>(M + H)+ |
| 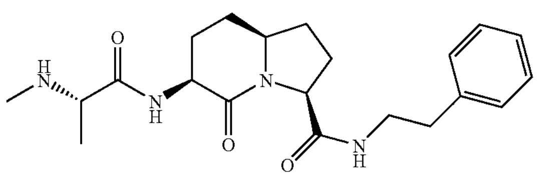 | Example 9<br>MS ESI 387.50<br>(M + H)+ |
| 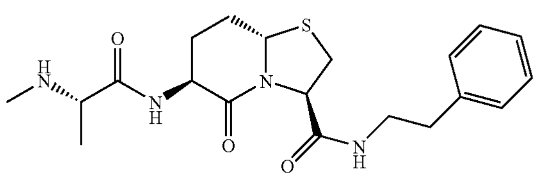 | Example 10<br>MS ESI 405.54<br>(M + H)+ |
| 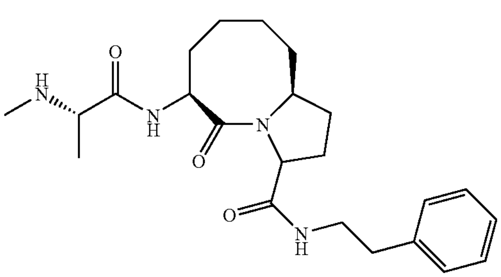 | Example 11<br>MS ESI 415.55<br>(M + H)+ |

-continued
| Compound Structure | Example Number |
|---|---|
| 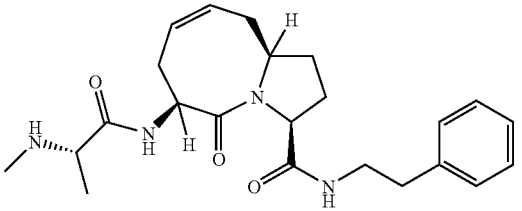 | Example 12<br>MS ESI 413.54<br>(M + H)+ |
| 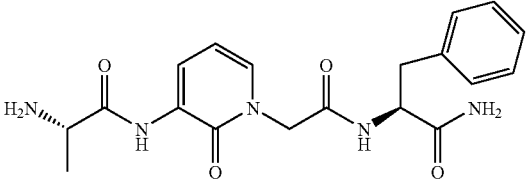 | Example 13<br>MS ESI 386.43<br>(M + H)+ |
| 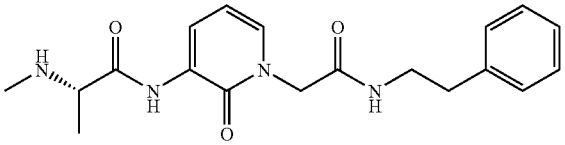 | Example 14<br>MS ESI 357.43<br>(M + H)+ |
| 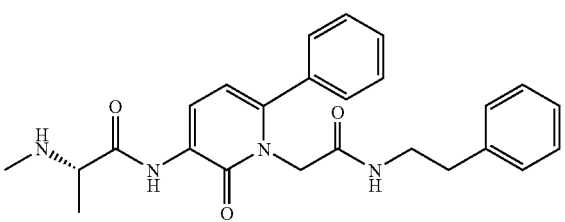 | Example 15<br>MS ESI 433.53<br>(M + H)+ |
| 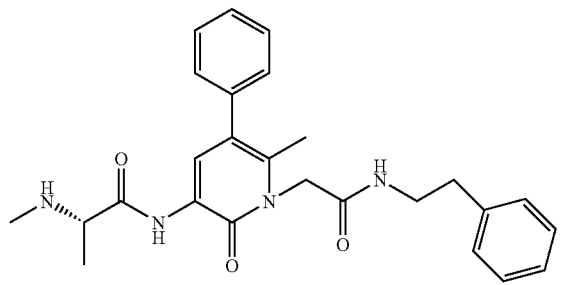 | Example 16<br>MS ESI 447.55<br>(M + H)+ |
| 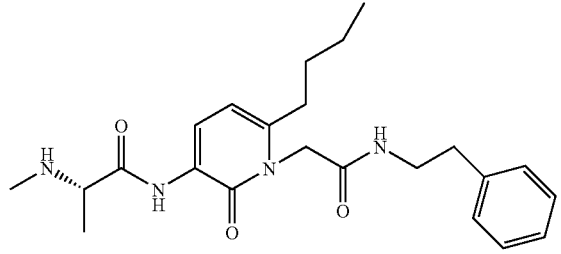 | Example 17<br>MS ESI 413.54<br>(M + H)+ |
| 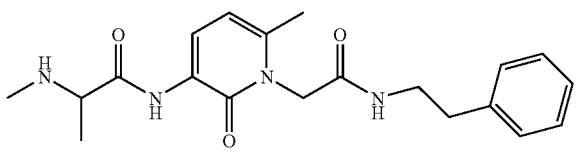 | Example 18<br>MS ESI 371.46<br>(M + H)+ |

-continued

| Compound Structure | Example Number |
|---|---|
| 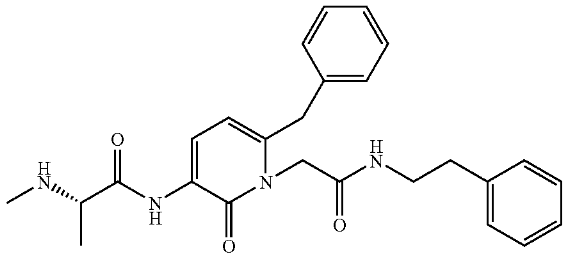 | Example 19<br>MS ESI 447.55<br>(M + H)+ |
| 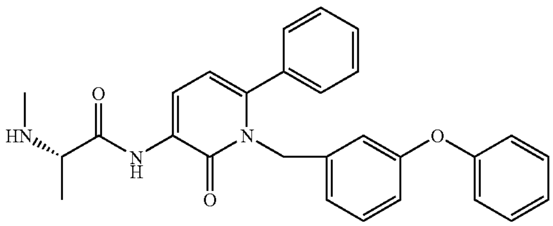 | Example 20<br>MS ESI 454.55<br>(M + H)+ |
| 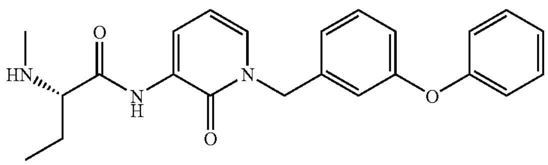 | Example 21<br>MS ESI 392.47<br>(M + H)+ |
| 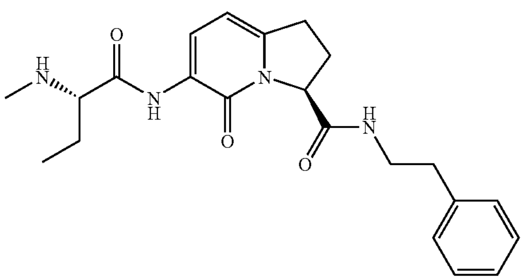 | Example 22<br>MS ESI 397.49<br>(M + H)+ |
| 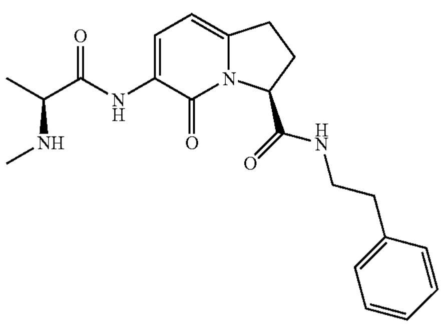 | Example 23<br>MS ESI 383.47<br>(M + H)+ |
| 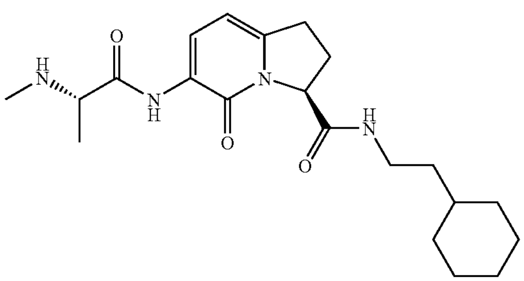 | Example 24<br>MS ESI 389.51<br>(M + H)+ |

-continued

| Compound Structure | Example Number |
|---|---|
| 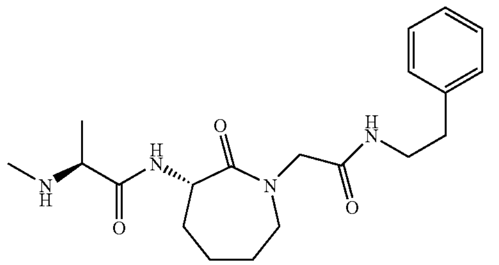 | Example 25<br>MS ESI 375.49<br>$(M + H)^+$ |
| 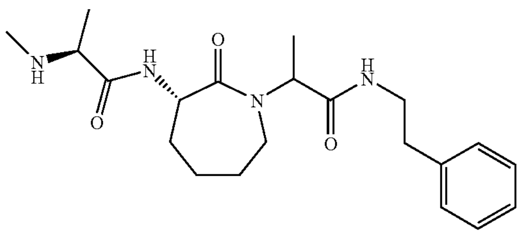 | Example 26<br>MS ESI 389.2<br>$(M + H)^+$ |
| 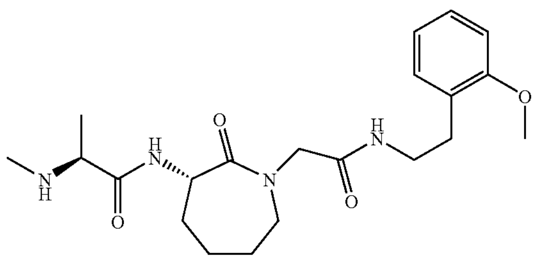 | Example 27<br>MS ESI 405.51<br>$(M + H)^+$ |
| 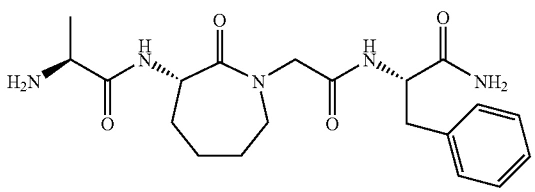 | Example 28<br>MS ESI 404.49<br>$(M + H)^+$ |
| 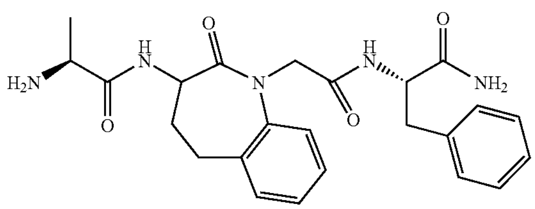 | Example 29<br>MS ESI 452.53<br>$(M + H)^+$ |
| 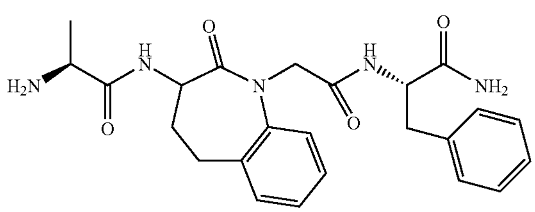 | Example 30<br>MS ESI 452.53<br>$(M + H)^+$ |
| 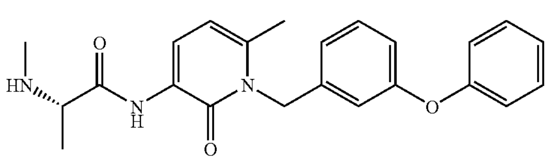 | Example 31<br>MS ESI 392.47<br>$(M + H)^+$ |

| Compound Structure | Example Number |
|---|---|
| (structure) | Example 32<br>MS ESI 378.17<br>(M + H)+ |

In order to measure the ability of the inventive compounds to bind the BIR3 peptide binding pocket, a solution phase assay on the FMAT or ELISA technology platform is utilized.

Fmat

Biotinylated Smac 7-mer peptide (AVPIAQK, lysine ε-amino group is biotinylated) is immobilized on streptavidin coated beads. GST-BIR3 fusion protein is precipitated with FMAT beads and is detected using fluorescent tagged anti-GST antibodies. Importantly, non-biotinylated Smac peptide is highly effective at competing GST-BIR3 off the FMAT beads (FIG. 2). The $IC_{50}$ for non-biotinylated Smac is 400 nM. The $IC_{50}$ values of compounds listed in Table 1 in the described FMAT assay ranged from 0.025-10 μM.

Elisa

Compounds are incubated with GST-BIR3 fusion protein and biotinylated SMAC peptide (AVPFAQK) in stretavidin-coated 96-well plates. For XIAP BIR3 Smac Elisa, a GST-BIR3 fusion containing amino acids 248-358 from XIAP was used. For CIAP1 BIR3 Smac Elisa, a GST-BIR3 fusion containing amino acids 259-364 from CIAP1 was used. Following a 30-minute incubation, wells are extensively washed. The remaining GST-BIR3 fusion protein is monitored by ELISA assay involving first, incubation with goat anti-GST antibodies followed by washing and incubation with alkaline phosphatase conjugated anti-goat antibodies. Signal is amplified using Attophos (Promega) and read with Cytoflour Ex 450 nm/40 and Em 580 nm. $IC_{50}$s correspond to concentration of compound which displaces half of GST-BIR3 signal. The $IC_{50}$ for non-biotinylated Smac is 400 nM. The $IC_{50}$ values of compounds listed in Table 1 in the described ELISA assays ranged from 0.005-10 μM.

Cell Proliferation Assay

The ability of compounds to inhibit tumor cell growth in vitro was monitored using the CellTiter 96® AQ$_{ueous}$ Non-Radioactive Cell Proliferation Assay (Promega). This assay is composed of solutions of a novel tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine methosulfate) PMS. MTS is bioreduced by cells into a formazan product, the absorbance of which is measured at 490 nm. The conversion of MTS into the aqueous soluble formazan product is accomplished by dehydrogenase enzymes found in metabolically active cells. The quantity of formazan product as measured by the amount of 490 nm absorbance is directly proportional to the number of living cells in culture. The $IC_{50}$ values of compounds listed in Table 1 in the described cell assays ranged from 0.005-50 μM.

Table 2

| Compound Structure | Example Number |
|---|---|
| (structure) | Example 33<br>MS ESI 484.2<br>(M + H)+ |
| (structure) | Example 34<br>MS ESI 498.2<br>(M + H)+ |

-continued

| Compound Structure | Example Number |
|---|---|
| | Example 35<br>MS ESI 471.2<br>(M + H)⁺ |
| | Example 36<br>MS ESI 485.2<br>(M + H)⁺ |
| | Example 37<br>MS ESI 485.2<br>(M + H)⁺ |
| | Example 38<br>MS ESI 499.2<br>(M + H)⁺ |
| | Example 39<br>MS ESI 488.2<br>(M + H)⁺ |
| | Example 40<br>MS ESI 520.2<br>(M + H)⁺ |

-continued

| Compound Structure | Example Number |
|---|---|
| 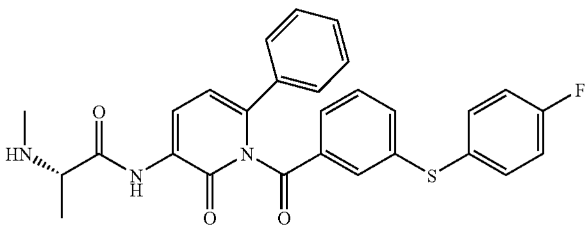 | Example 41<br>MS ESI 502.2<br>(M + H)+ |
| 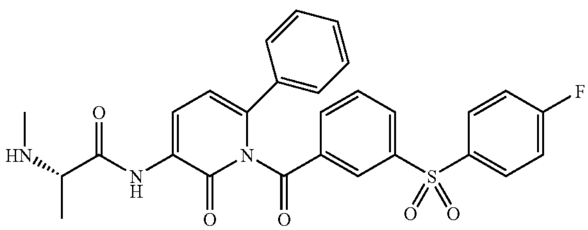 | Example 42<br>MS ESI 534.1<br>(M + H)+ |
| 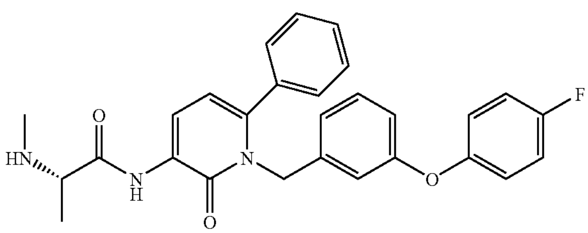 | Example 43<br>MS ESI 472.2<br>(M + H)+ |
| 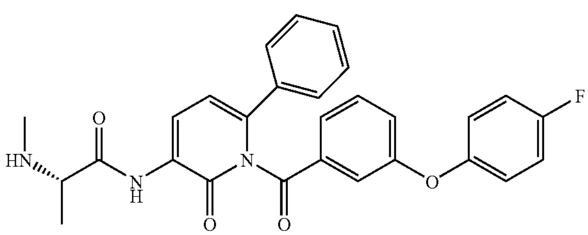 | Example 44<br>MS ESI 486.2<br>(M + H)+ |
| 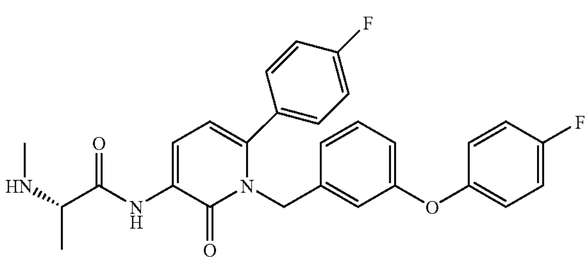 | Example 45<br>MS ESI 490.2<br>(M + H)+ |
| 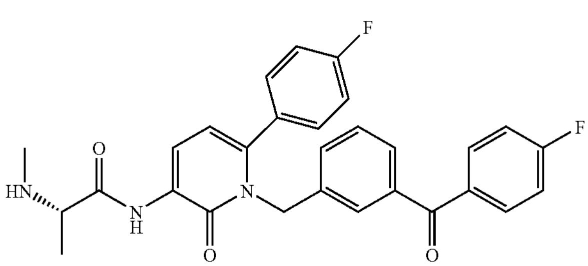 | Example 46<br>MS ESI 502.8<br>(M + H)+ |

| Compound Structure | Example Number |
|---|---|
| | Example 47<br>MS ESI 489.2<br>$(M + H)^+$ |
| | Example 48<br>MS ESI 503.2<br>$(M + H)^+$ |
| | Example 49<br>MS ESI 506.2<br>$(M + H)^+$ |
| | Example 50<br>MS ESI 538.2<br>$(M + H)^+$ |
| | Example 51<br>MS ESI 527.2<br>$(M + H)^+$ |

-continued

| Compound Structure | Example Number |
|---|---|
| | Example 52<br>MS ESI 555.3<br>$(M + H)^+$ |
| | Example 53<br>MS ESI 477.2<br>$(M + H)^+$ |
| | Example 54<br>MS ESI 458.2<br>$(M + H)^+$ |
| | Example 55<br>MS ESI 437.2<br>$(M + H)^+$ |
| | Example 56<br>MS ESI 455.2<br>$(M + H)^+$ |

| Compound Structure | Example Number |
|---|---|
| 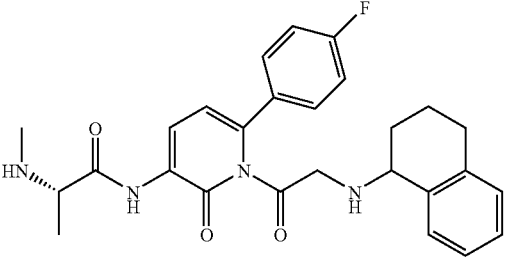 | Example 57<br>MS ESI 477.2<br>$(M + H)^+$ |
| 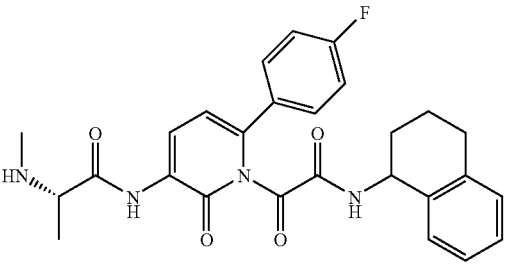 | Example 58<br>MS ESI 491.2<br>$(M + H)^+$ |
| 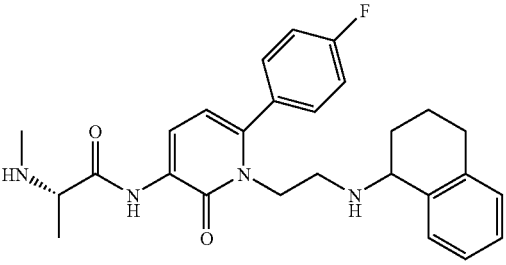 | Example 59<br>MS ESI 463.2<br>$(M + H)^+$ |
| 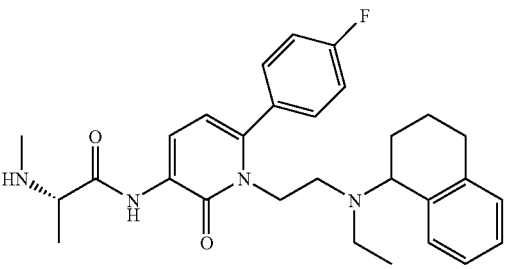 | Example 60<br>MS ESI 491.3<br>$(M + H)^+$ |
| 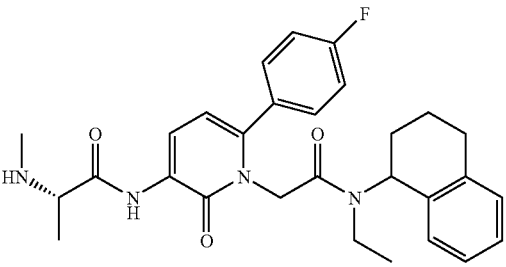 | Example 61<br>MS ESI 505.3<br>$(M + H)^+$ |

-continued

| Compound Structure | Example Number |
|---|---|
| | Example 62<br>MS ESI 505.3<br>(M + H)+ |
| | Example 63<br>MS ESI 483.2<br>(M + H)+ |
| | Example 64<br>MS ESI 468.2<br>(M + H)+ |
| | Example 65<br>MS ESI 432.2<br>(M + H)+ |
| | Example 66<br>MS ESI 436.2<br>(M + H)+ |
| | Example 67<br>MS ESI 468.2<br>(M + H)+ |

-continued
| Compound Structure | Example Number |
|---|---|
| 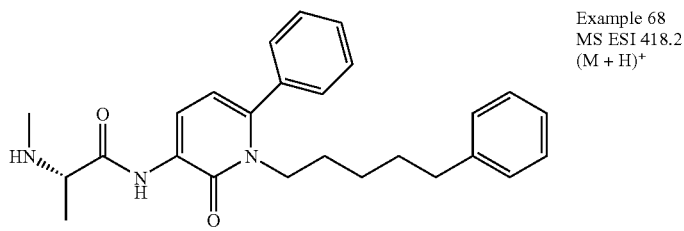 | Example 68<br>MS ESI 418.2<br>(M + H)+ |
| 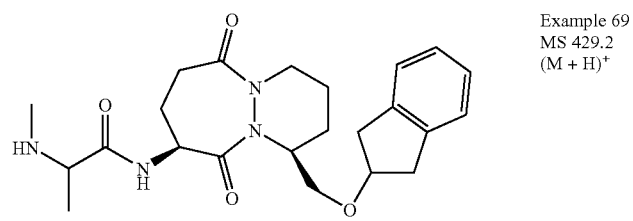 | Example 69<br>MS 429.2<br>(M + H)+ |
| 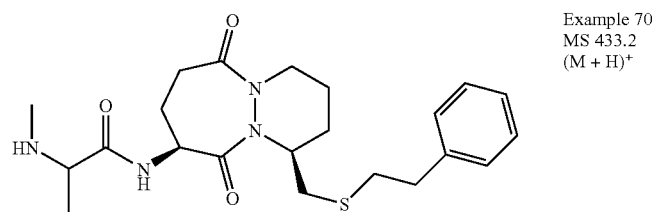 | Example 70<br>MS 433.2<br>(M + H)+ |
| 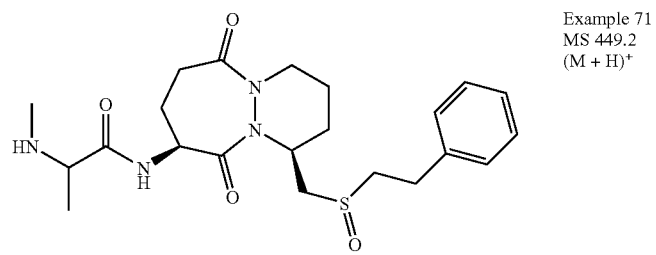 | Example 71<br>MS 449.2<br>(M + H)+ |
| 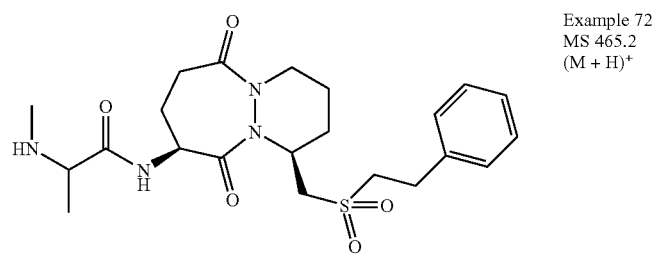 | Example 72<br>MS 465.2<br>(M + H)+ |
| 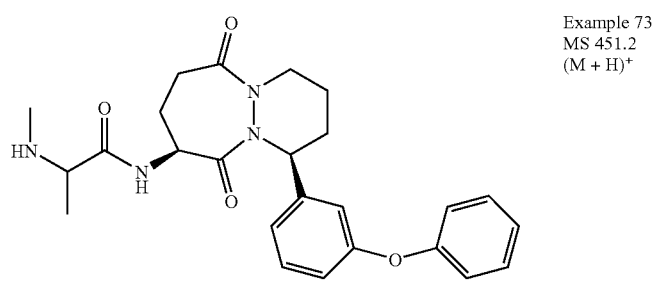 | Example 73<br>MS 451.2<br>(M + H)+ |

| Compound Structure | Example Number |
|---|---|
| 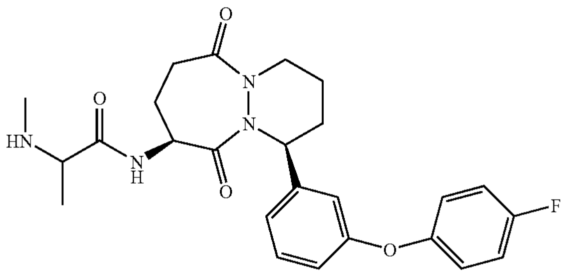 | Example 74<br>MS 469.2<br>(M + H)+ |
| 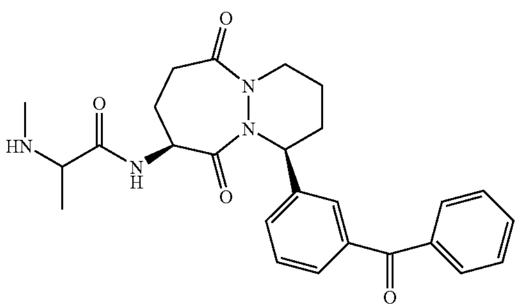 | Example 75<br>MS 463.2<br>(M + H)+ |
| 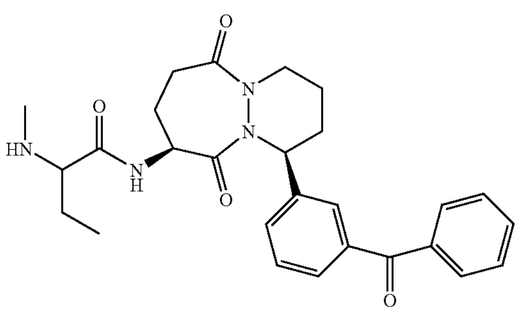 | Example 76<br>MS 476.2<br>(M + H)+ |
| 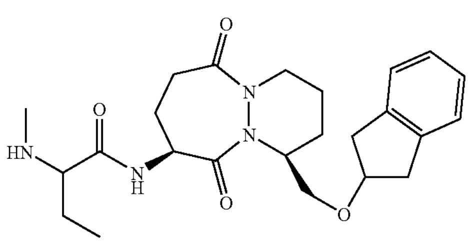 | Example 77<br>MS 443.3<br>(M + H)+ |
| 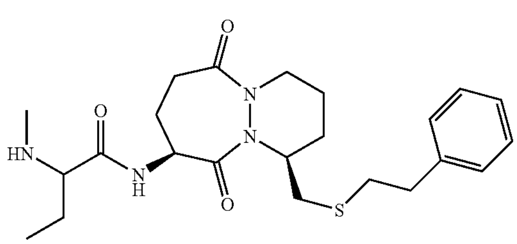 | Example 78<br>MS 447.2<br>(M + H)+ |

-continued

| Compound Structure | Example Number |
| --- | --- |
| 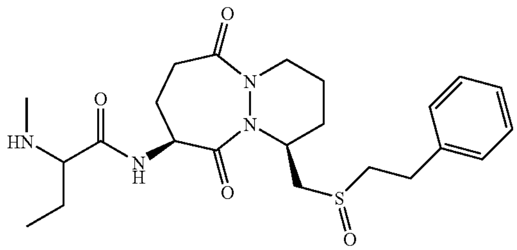 | Example 79<br>MS 463.2<br>(M + H)+ |
| 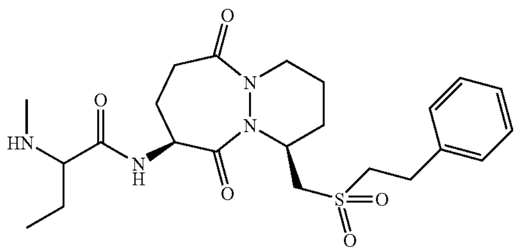 | Example 80<br>MS 479.2<br>(M + H)+ |
| 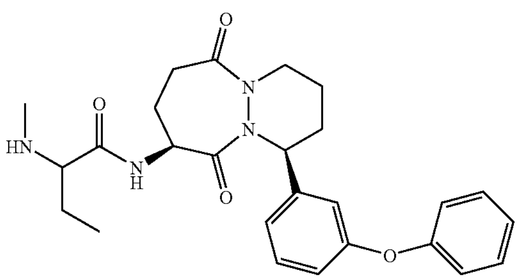 | Example 81<br>MS 465.2<br>(M + H)+ |
| 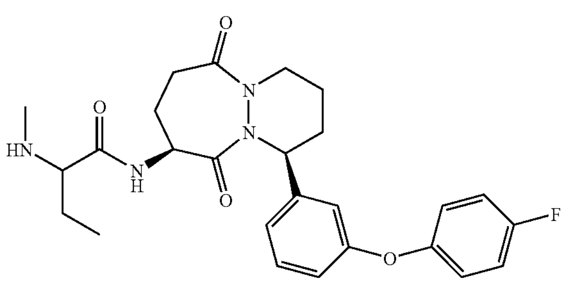 | Example 82<br>MS 483.2<br>(M + H)+ |
| 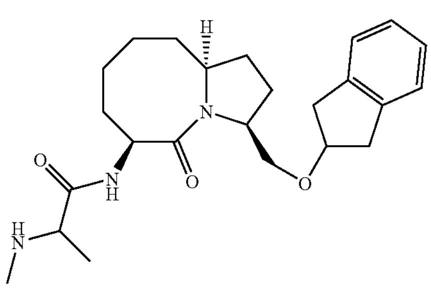 | Example 83<br>MS 414.3<br>(M + H)+ |

| Compound Structure | Example Number |
|---|---|
| | Example 84<br>MS 418.3<br>$(M + H)^+$ |
| | Example 85<br>MS 434.2<br>$(M + H)^+$ |
| | Example 86<br>MS 450.2<br>$(M + H)^+$ |
| | Example 87<br>MS 436.3<br>$(M + H)^+$ |
| | Example 88<br>MS 454.2<br>$(M + H)^+$ |

-continued
| Compound Structure | Example Number |
|---|---|
| 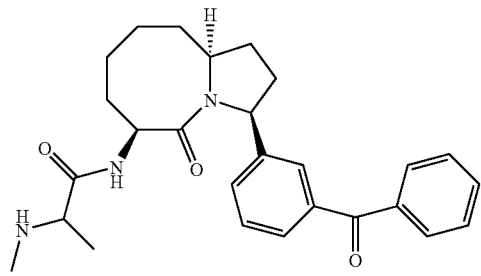 | Example 89<br>MS 448.3<br>$(M + H)^+$ |
| 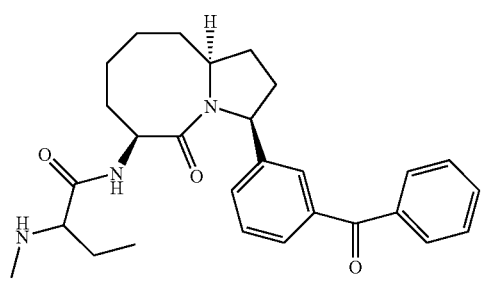 | Example 90<br>MS 462.3<br>$(M + H)^+$ |
| 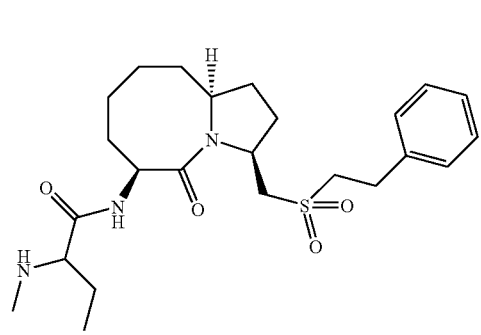 | Example 91<br>MS 464.3<br>$(M + H)^+$ |
| 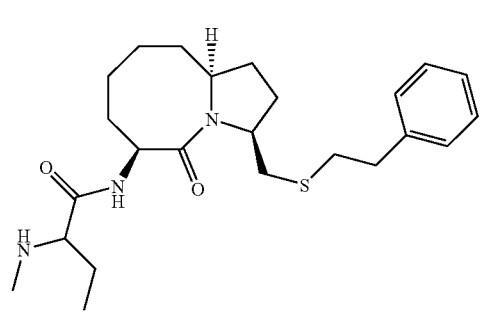 | Example 92<br>MS 432.3<br>$(M + H)^+$ |
| 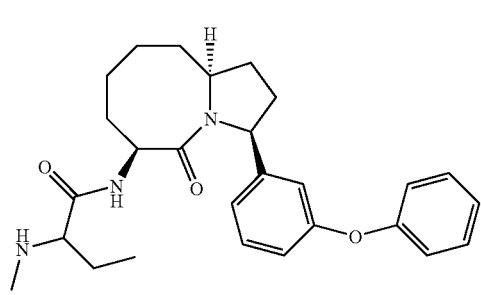 | Example 93<br>MS 450.3<br>$(M + H)^+$ |

-continued

| Compound Structure | Example Number |
|---|---|
| 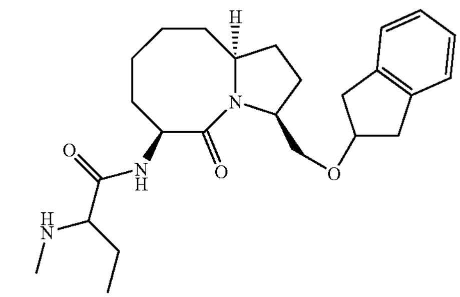 | Example 94<br>MS 428.3<br>$(M + H)^+$ |
| 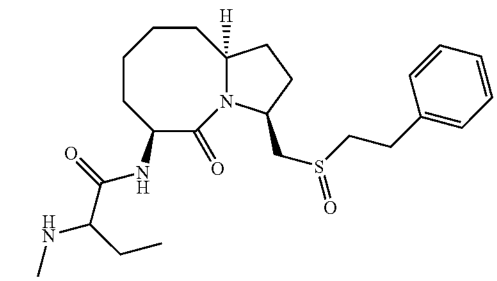 | Example 95<br>MS 464.3<br>$(M + H)^+$ |
| 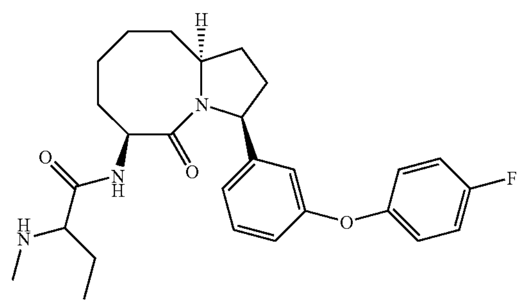 | Example 96<br>MS 468.3<br>$(M + H)^+$ |
| 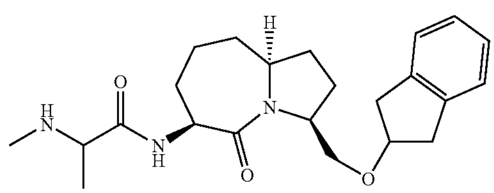 | Example 97<br>MS 400.3<br>$(M + H)^+$ |
| 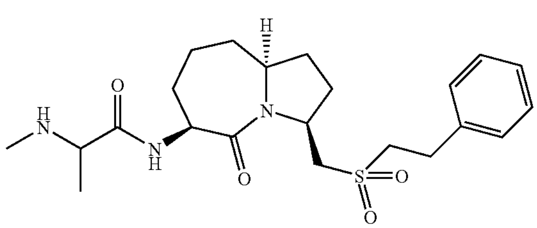 | Example 98<br>MS 436.2<br>$(M + H)^+$ |
| 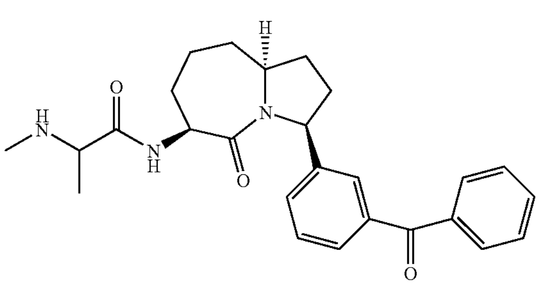 | Example 99<br>MS 434.2<br>$(M + H)^+$ |

| Compound Structure | Example Number |
|---|---|
| 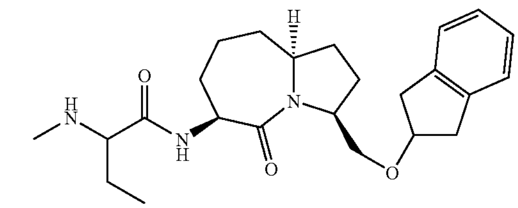 | Example 100<br>MS 430.3<br>(M + H)+ |
| 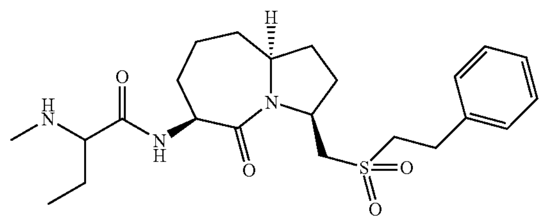 | Example 101<br>MS 450.2<br>(M + H)+ |
| 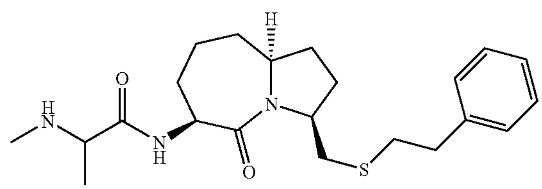 | Example 102<br>MS 404.2<br>(M + H)+ |
| 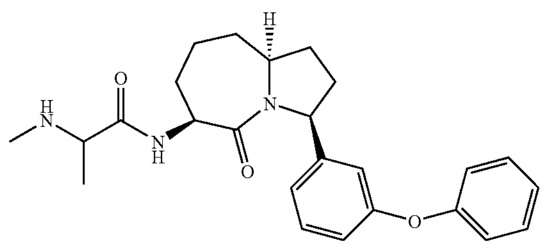 | Example 103<br>MS 422.2<br>(M + H)+ |
| 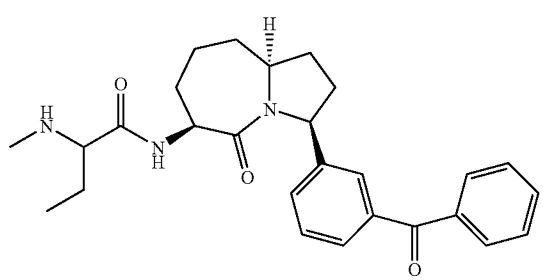 | Example 104<br>MS 448.3<br>(M + H)+ |
| 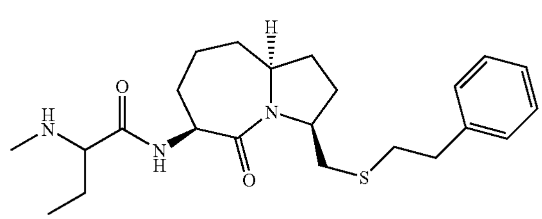 | Example 105<br>MS 418.2<br>(M + H)+ |

-continued

| Compound Structure | Example Number |
|---|---|
| | Example 106<br>MS 436.3<br>(M + H)⁺ |
| | Example 107<br>MS 420.2<br>(M + H)⁺ |
| | Example 108<br>MS 440.2<br>(M + H)⁺ |
| | Example 109<br>MS 434.2<br>(M + H)⁺ |
| | Example 110<br>MS 454.2<br>(M + H)⁺ |
| | Example 111<br>MS 386.2<br>(M + H)⁺ |

| Compound Structure | Example Number |
|---|---|
| 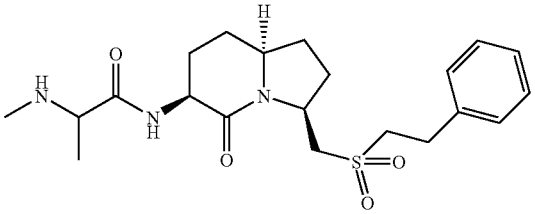 | Example 112<br>MS 422.2<br>(M + H)+ |
| 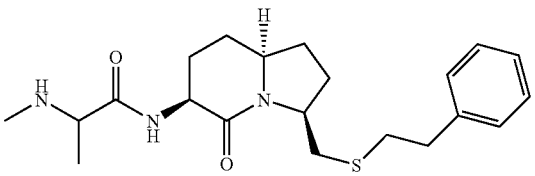 | Example 113<br>MS 390.2<br>(M + H)+ |
| 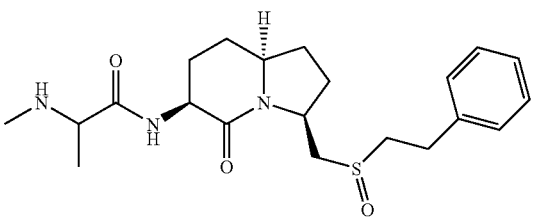 | Example 114<br>MS 406.2<br>(M + H)+ |
| 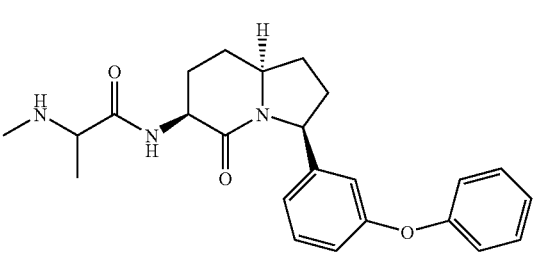 | Example 115<br>MS 408.2<br>(M + H)+ |
| 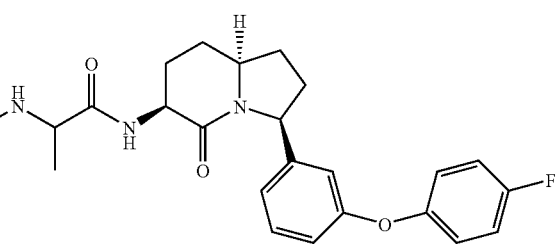 | Example 116<br>MS 426.2<br>(M + H)+ |
| 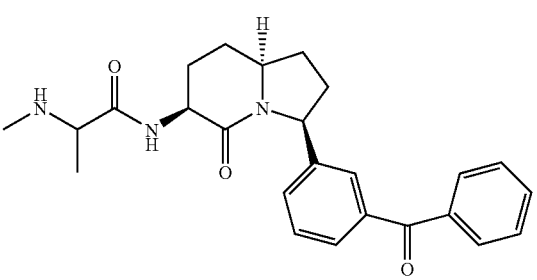 | Example 117<br>MS 420.2<br>(M + H)+ |

-continued

| Compound Structure | Example Number |
|---|---|
| 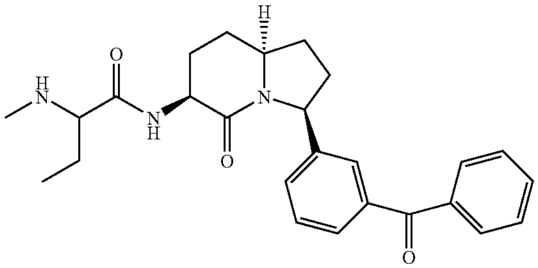 | Example 118<br>MS 434.2<br>(M + H)+ |
| 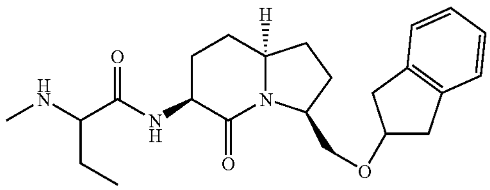 | Example 119<br>MS 400.2<br>(M + H)+ |
| 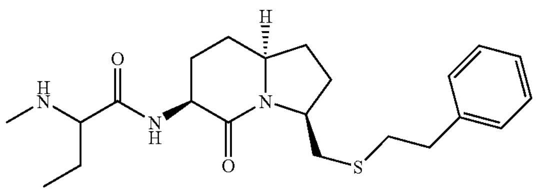 | Example 120<br>MS 404.2<br>(M + H)+ |
| 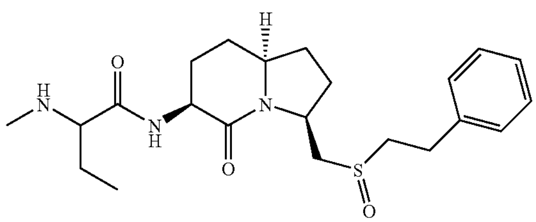 | Example 121<br>MS 420.2<br>(M + H)+ |
| 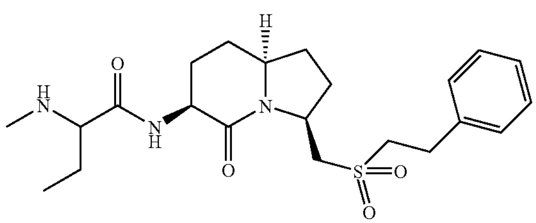 | Example 122<br>MS 436.2<br>(M + H)+ |
| 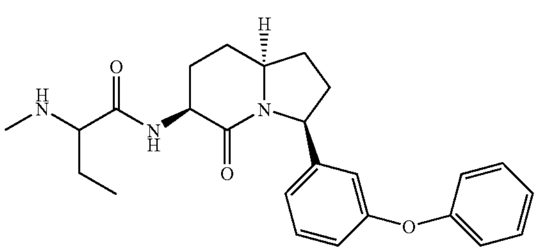 | Example 123<br>MS 422.2<br>(M + H)+ |

-continued

| Compound Structure | Example Number |
|---|---|
|  | Example 124<br>MS 440.2<br>(M + H)⁺ |
|  | Example 125<br>MS 427.2<br>(M + H)⁺ |
|  | Example 126<br>MS ESI 430.2<br>(M + H)⁺ |
|  | Example 127<br>MS ESI 444.2<br>(M + H)⁺ |
|  | Example 128<br>MS ESI 498.3<br>(M + H)⁺ |
|  | Example 129<br>MS ESI 512.3<br>(M + H)⁺ |

| Compound Structure | Example Number |
|---|---|
| 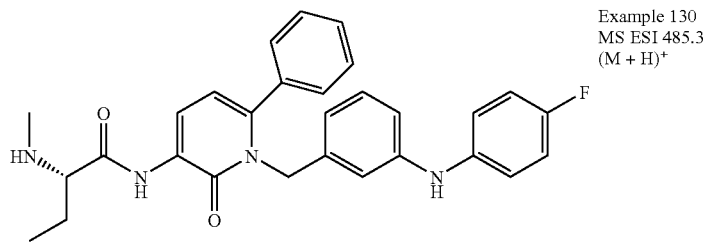 | Example 130<br>MS ESI 485.3<br>$(M + H)^+$ |
| 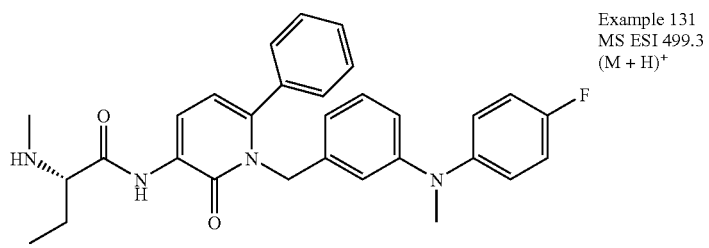 | Example 131<br>MS ESI 499.3<br>$(M + H)^+$ |
| 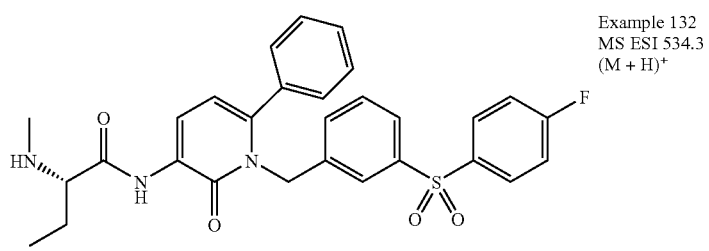 | Example 132<br>MS ESI 534.3<br>$(M + H)^+$ |
| 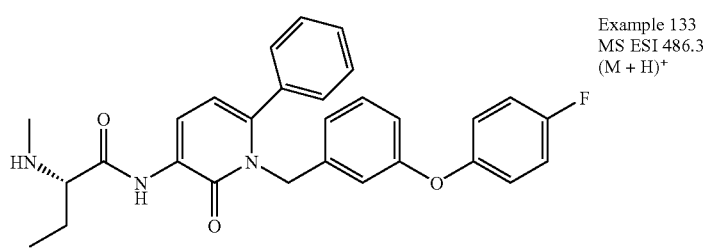 | Example 133<br>MS ESI 486.3<br>$(M + H)^+$ |
| 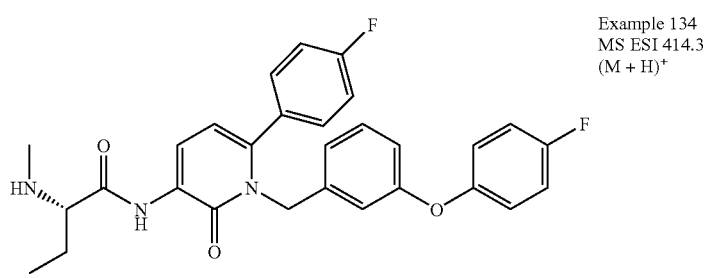 | Example 134<br>MS ESI 414.3<br>$(M + H)^+$ |
| 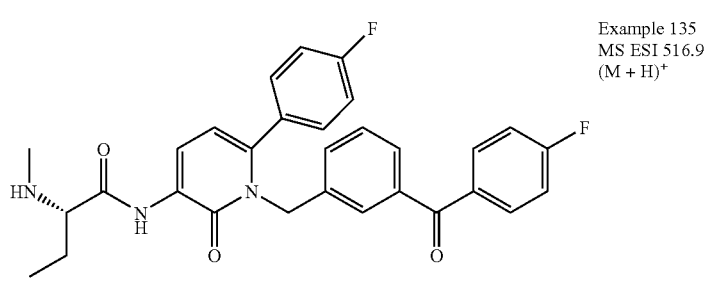 | Example 135<br>MS ESI 516.9<br>$(M + H)^+$ |

| Compound Structure | Example Number |
|---|---|
| 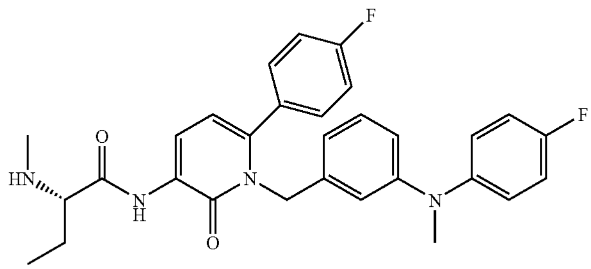 | Example 136<br>MS ESI 517.3<br>(M + H)+ |
| 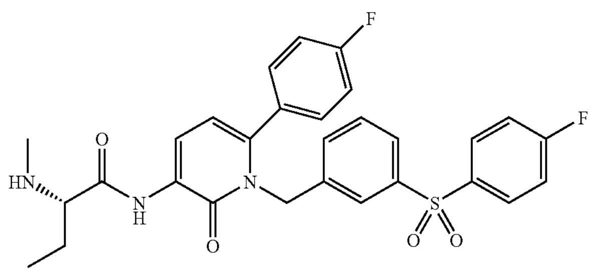 | Example 137<br>MS ESI 552.3<br>(M + H)+ |
| 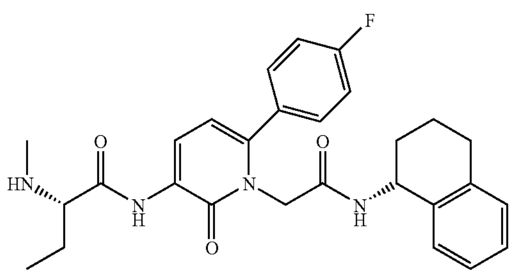 | Example 138<br>MS ESI 491.3<br>(M + H)+ |
| 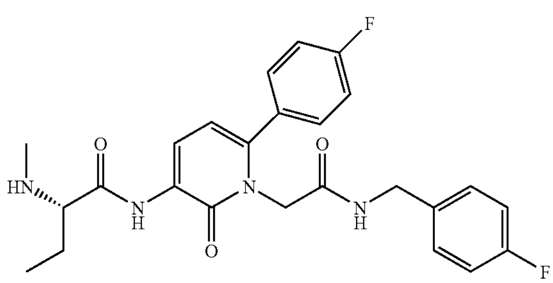 | Example 139<br>MS ESI 469.3<br>(M + H)+ |
| 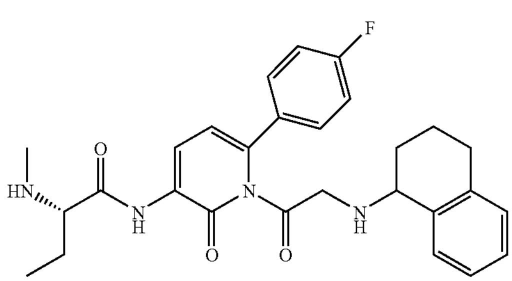 | Example 140<br>MS ESI 491.3<br>(M + H)+ |

-continued

| Compound Structure | Example Number |
|---|---|
| | Example 141<br>MS ESI 519.4<br>(M + H)⁺ |
| | Example 142<br>MS ESI 497.3<br>(M + H)⁺ |
| | Example 143<br>MS ESI 446.3<br>(M + H)⁺ |
| | Example 144<br>MS ESI 482.3<br>(M + H)⁺ |

We claim:

1. A compound of the formula (II):

$$\text{(II)}$$

wherein $R_1$ is H or $C_1$-$C_4$ alkyl;

$R_2$ is H, or $C_1$-$C_4$ alkyl which is unsubstituted or substituted by one or more substituents selected from halogen, —OH, —SH, —OCH$_3$, —SCH$_3$, —CN, —SCN and nitro;

$R_3$ is H, $C_1$-$C_4$ alkyl, —CF$_3$, —C$_2$F$_5$, —CH$_2$—Z or $R_2$ and $R_3$ together form with the nitrogen form a $C_3$-$C_6$ heteroaliphatic ring;

Z is H, —OH, F, Cl, —CH$_3$; —CF$_3$, —CH$_2$Cl, —CH$_2$F or —CH$_2$OH;

X is a monocyclic structure selected from the group consisting of

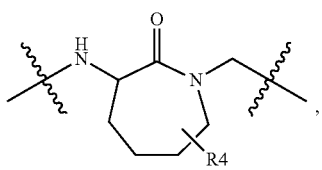

85

-continued

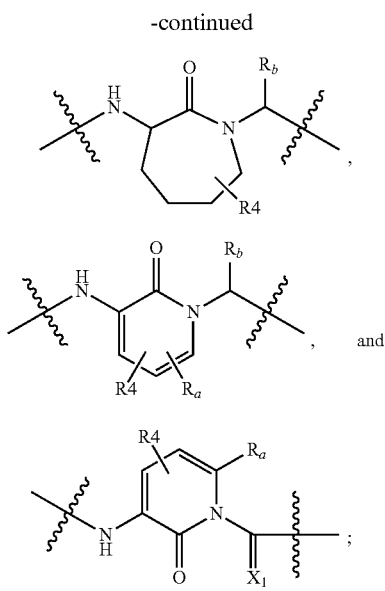

where
- A is —CH$_2$, —CH—, N, O, or S;
- X$_1$ is O, S, or NR$_a$;
- R$_4$, R$_a$ and R$_b$ are independently, H; C$_1$-C$_{16}$ straight or branched alkyl; C$_1$-C$_{16}$ alkenyl; C$_1$-C$_{16}$ alkynyl; or C$_1$-C$_{16}$ cycloalkyl; —(CH$_2$)$_{0-6}$-phenyl; (CH$_2$)$_{0-6}$-het; —O—C$_1$-C$_{16}$ straight or branched alkyl, —S—C$_1$-C$_{16}$ straight or branched alkyl; —N—C$_1$-C$_{16}$ straight or branched alkyl; —O—C$_1$-C$_{16}$ alkenyl; —S—C$_1$-C$_{16}$ alkenyl; —N—C$_1$-C$_{16}$ alkenyl —O—C$_1$-C$_{16}$ cycloalkyl; —N—C$_1$-C$_{16}$ cycloalkyl; —S—C$_1$-C$_{16}$ cycloalkyl; —O—(CH$_2$)$_{0-6}$-phenyl; —N—(CH$_2$)$_{0-6}$-phenyl; —S—(CH$_2$)$_{0-6}$-phenyl; —O—(CH$_2$)$_{0-6}$-het; —N—(CH$_2$)$_{0-6}$-het or —S—(CH$_2$)$_{0-6}$-het wherein alkyl, cycloalkyl and phenyl are unsubstituted or substituted; or R$_4$ and R$_a$ may form a ring;
- U is —R$_5$; —CH(R$_5$)(R$_6$); —CO—N(R$_5$)(R$_6$); —CO—O(R$_5$); —CO—S(R$_5$); —CS—N(R$_5$)(R$_6$); —N(R$_5$)—CO—N(R$_5$)(R$_6$); —C$_1$-C$_5$ alkyl-N(R$_5$)(R$_6$); —C$_1$-C$_5$-alkyl-O(R$_6$) or —C$_1$-C$_5$ alkyl-S(O)$_n$(R$_6$) where n is 0, 1 or 2;
- R$_5$ is H; C$_1$-C$_{10}$ alkyl; C$_3$-C$_7$ cycloalkyl; —(CH$_2$)$_{1-6}$—C$_3$-C$_7$ cycloalkyl; —C$_1$-C$_{10}$ alkyl-aryl; —(CH$_2$)$_{0-6}$-phenyl; —(CH$_2$)$_{0-6}$—C$_3$-C$_7$ cycloalkyl-(CH$_2$)$_{0-6}$-phenyl; —(CH$_2$)$_{0-4}$CH—((CH$_2$)$_{1-4}$-phenyl)$_2$; —(CH$_2$)$_{0-6}$—CH(phenyl)$_2$; —C(O)—C$_1$-C$_{10}$ alkyl; —C(O)—(CH$_2$)$_{1-6}$—C$_3$-C$_7$ cycloalkyl; —C(O)—(CH$_2$)$_{0-6}$-phenyl; —(CH$_2$)$_{1-6}$-het; —C(O)—(CH$_2$)$_{1-6}$-het; —(CR$_7$R$_8$)$_{0-2}$-Aryl-V-Aryl; CHR$_6$C(O)N(R$_{12}$)(R$_{13}$); C(O)—NH—CH(R$_{11}$)(R$_{14}$) or R$_5$ is a residue of an amino acid, wherein the alkyl, cycloalkyl, phenyl and aryl substituents are unsubstituted or substituted;
- or when U is —CO—N(R$_5$)(R$_6$); —CS—N(R$_5$)(R$_6$); —N(R$_5$)—CO—N(R$_5$)(R$_6$); or N(R$_5$)—CO—N(R$_5$)(R$_6$), R$_5$ and R$_6$ together with the N atom form an aromatic or aliphatic heterocycle;
- R$_7$ and R$_8$ are independently H, halogen; C$_{1-7}$ alkyl; —OC$_{1-7}$ alkyl; C$_{1-7}$ cycloalkyl; or —OC$_{1-7}$ cycloalkyl wherein the alkyl, cycloalkyl substituents may be substituted or unsubstituted;
- V is R$_9$; R$_{10}$; CR$_9$R$_{10}$; —C(O)—; C(hal)$_2$; —O—; —N(H)—; N(alkyl); N(aryl); S; SO; or S(O)$_2$;
- R$_9$ and R$_{10}$ are independently H, halogen, C$_{1-7}$ alkyl; —OC$_{1-7}$ alkyl; C$_{1-7}$ cycloalkyl; or —OC$_{1-7}$ cycloalkyl wherein the alkyl, cycloalkyl substituents may be substituted or unsubstituted;
- R$_6$ is H; —C$_1$-C$_{10}$ alkyl; —OH; —O—C$_1$-C$_{10}$ alkyl; —(CH$_2$)$_{0-6}$—C$_3$-C$_7$ cycloalkyl; —O—(CH$_2$)$_{0-6}$-aryl; —(CH$_2$)$_{0-6}$-aryl; phenyl; —(CH$_2$)$_{1-6}$-het; —O—(CH$_2$)$_{1-6}$-het; —N(R$_{12}$)(R$_{13}$); —CNOR$_{12}$; —S—R$_{12}$; —S(O)—R$_{12}$; —S(O)$_2$—R$_{12}$; or —S(O)$_2$—NR$_{12}$R$_{13}$ wherein the alkyl, cycloalkyl and aryl substituents are unsubstituted or substituted;
- R$_{12}$ and R$_{13}$ are independently H; C$_1$-C$_{10}$ alkyl; —(CH$_2$)$_{0-6}$—C$_3$-C$_7$ cycloalkyl; —(CH$_2$)$_{0-6}$—(CH)$_{0-1}$(aryl)$_{1-2}$; —C(O)—C$_1$-C$_{10}$ alkyl; —C(O)—(CH$_2$)$_{1-6}$—C$_3$-C$_7$ cycloalkyl; —C(O)—O—(CH$_2$)$_{0-6}$-aryl; —C(O)—(CH$_2$)$_{0-6}$—O-fluorenyl; —C(O)—NH—(CH$_2$)$_{0-6}$-aryl; —C(O)—(CH$_2$)$_{0-6}$-aryl; or —C(O)—(CH$_2$)$_{1-6}$-het, wherein the alkyl, cycloalkyl and aryl substituents are unsubstituted or substituted; or a substituent that facilitates transport of the molecule across a cell membrane, or R$_{12}$ and R$_{13}$ together with the nitrogen are het;
- where R$_{11}$ and R$_{14}$ are C$_{1-7}$ alkyl; —(CH$_2$)$_{0-6}$-phenyl; or amide;
- aryl is phenyl, naphthyl, or indanyl which is unsubstituted or substituted;

or a pharmaceutically acceptable salt thereof.

2. A compound of formula (II) according to claim 1 wherein
- R$_1$ is H or C$_1$-C$_4$ alkyl;
- R$_2$ is H or C$_1$-C$_4$ alkyl;
- R$_3$ is H or C$_1$-C$_4$ alkyl;
- X is a monocyclic selected from the group consisting of

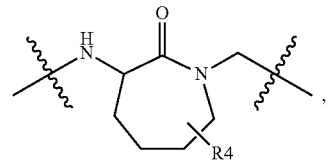

1

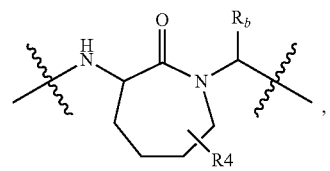

2

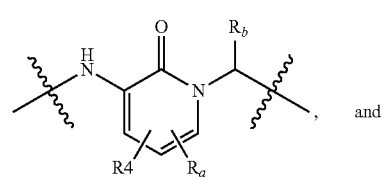

, and

4

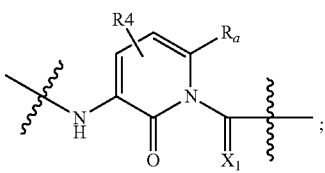

;

13 where
- A is —CH$_2$, —CH—, N, O, or S;
- X$_1$ is O, S, or NR$_a$;

$R_4$, $R_a$ and $R_b$ are independently, H; $C_1$-$C_{16}$ straight or branched alkyl; or —$(CH_2)_{0-6}$-phenyl wherein phenyl is unsubstituted with halo;

U is —$R_5$; —$CH(R_5)(R_6)$; $C_1$-$C_5$ alkyl-$N(R_5)(R_6)$; or —CO—$N(R_5)(R_6)$;

$R_5$ is H; $C_1$-$C_{10}$ alkyl; —$(CH_2)_{0-6}$-phenyl; —C(O)—$C_1$-$C_{10}$alkyl; —C(O)—$(CH_2)_{0-6}$-phenyl; —$(CR_7R_8)_{0-2}$-Aryl-V-Aryl; $CHR_6C(O)N(R_{12})(R_{13})$; or C(O)—NH—$CH(R_{11})(R_{14})$;

$R_7$ and $R_8$ are independently H, halogen; $C_{1-7}$ alkyl; —$OC_{1-7}$ alkyl; $C_{1-7}$ cycloalkyl; or —$OC_{1-7}$ cycloalkyl;

V is —C(O)—; $C(hal)_2$; —O—; —N(H)—; N(alkyl); N(aryl); S; SO; or $S(O)_2$;

$R_9$ and $R_{10}$ are independently H, halogen, $C_{1-7}$ alkyl; —$OC_{1-7}$ alkyl; $C_{1-7}$ cycloalkyl; or —$OC_{1-7}$ cycloalkyl;

$R_6$ is H; —$C_1$-$C_{10}$ alkyl; —OH; —O—$C_1$-$C_{10}$ alkyl; —$(CH_2)_{0-6}$-phenyl; —$(CH_2)_{0-6}$-aryl-; —O—$(CH_2)_{0-6}$-aryl;

phenyl; —$(CH_2)_{1-6}$-het; —O—$(CH_2)_{1-6}$-het; —$N(R_{12})(R_{13})$; —$CNOR_{12}$; —S—$R_{12}$; —S(O)—$R_{12}$; —$S(O)_2$—$R_{12}$; or —$S(O)_2$—$NR_{12}R_{13}$;

$R_{12}$ and $R_{13}$ are independently H, or $C_1$-$C_{10}$ alkyl;

where $R_{11}$ and $R_{14}$ are $C_{1-7}$ alkyl; —$(CH_2)_{0-6}$-phenyl; or amide;

aryl is phenyl, naphthyl, or indanyl which is unsubstituted or substituted;

or a pharmaceutically acceptable salt thereof.

3. A compound of formula (II) according to claim 1 wherein $R_1$, $R_2$ and $R_3$ are independently H or $C_1$-$C_4$ alkyl;

X is a monocyclic structure selected from the group consisting of

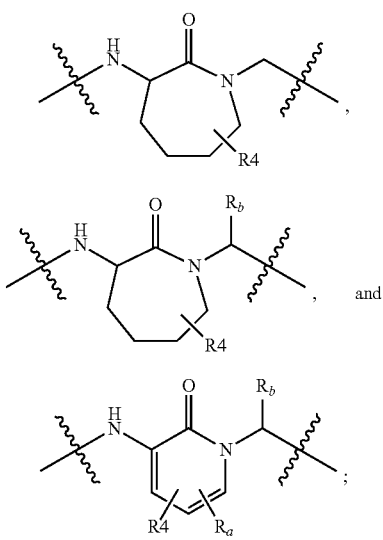

where
A is —$CH_2$, —CH—, N, O, or S;
$X_1$ is O, S, or $NR_a$;
$R_4$, $R_a$ and $R_b$ are independently, H; $C_1$-$C_{16}$ straight or branched alkyl; or —$(CH_2)_{0-6}$-phenyl;
U is —$R_5$; —CO—$N(R_5)(R_6)$ or $C_1$-$C_5$alkyl-$N(R_5)(R_6)$;
$R_5$ is H; —$(CH_2)_{0-6}$-phenyl; Aryl-V-Aryl; or C(O)—NH—$CH(R_{11})(R_{14})$ wherein aryl or phenyl may be substituted or unsubstituted;
V is —O—;

$R_6$ is H; —$C_1$-$C_{10}$ alkyl; —OH; —O—$C_1$-$C_{10}$ alkyl; —O—$(CH_2)_{0-6}$-phenyl; —$(CH_2)_{0-6}$-phenyl; indanyl or phenyl;

where $R_{11}$ and $R_{14}$ are $C_{1-7}$ alkyl; —$(CH_2)_{0-6}$-phenyl; or amide;

aryl is phenyl, naphthyl, or indanyl which is unsubstituted or substituted;

or a pharmaceutically acceptable salt thereof.

4. A compound selected from:
(S)-2-Amino-N-{1-[((S)-1-carbamoyl-2-phenyl-ethylcarbamoyl)-methyl]-2-oxo-1,2-dihydro-pyridin-3-yl}-propionamide;
(S)-2-Methylamino-N-[2-oxo-1-(phenethylcarbamoyl-methyl)-1,2-dihydro-pyridin-3-yl]-propionamide;
(S)-2-Methylamino-N-[2-oxo-1-(phenethylcarbamoyl-methyl)-6-phenyl-1,2-dihydro-pyridin-3-yl1]-propionamide;
2-Methylamino-N-[6-methyl-2-oxo-1-(phenethylcarbamoyl-methyl)-5-phenyl-1,2-dihydro-pyridin-3-yl]propionamide;
(S)-N-[6-Butyl-2-oxo-1-(phenethylcarbamoyl-methyl)-1,2-dihydro-pyridin-3-yl]-2-methylamino-propionamide;
2-Methylamino-N-[6-methyl-2-oxo-1-(phenethylcarbamoyl-methyl)-1,2-dihydro-pyridin-3-yl]-propionamide;
(S)-N-[6-Benzyl-2-oxo-1-(phenethylcarbamoyl-methyl)-1,2-dihydro-pyridin-3-yl]-2-methylamino-propionamide;
(S)-2-Methylamino-N-[2-oxo-1-(3-phenoxy-benzyl)-6-phenyl-1,2-dihydro-pyridin-3-yl]-propionamide;
(S)-2-Methylamino-N-[2-oxo-1-(3-phenoxy-benzyl)-1,2-dihydro-pyridin-3-yl]butyramide;
(S)-2-Methylamino-N-[(S)-2-oxo-1-(phenethylcarbamoyl-methyl)-azepan-3-yl]-propionamide;
2-[(S)-3-((S)-2-Methylamino-propionylamino)-2-oxo-azepan-1-yl]-N-phenethyl-propionamide;
(S)-N-((S)-1-{[2-(2-Methoxy-phenyl)-ethylcarbamoyl]-methyl}-2-oxo-azepan-3-yl)-2-methylamino-propionamine;
(S)-2-Amino-N-{(S)-1-[((S)-1-carbamoyl-2-phenyl-ethylcarbamoy)-methyl]-2-oxo-azepan-3-yl}-propionamide;
(S)-2-Methylamino-N-[6-methyl-2-oxo-1-(3-phenoxy-benzyl)-1,2-dihydro-pyridin-3-yl]-propionamide;
(S)-2-Methylamino-N-[2-oxo-1-(3-phenoxy-benzyl)-1,2-dihydro-pyridin-3-yl]-propionamide; and
(S)-N-[6-Phenyl-2-oxo-1-(3-phenoxy-benzyl)-1,2-dihydro-pyridin-3-yl]-2-methylamino-propionamide;

or a pharmaceutically acceptable salt thereof.

5. A compound selected from:
(S)—N-{1-[3-(4-Fluoro-benzoyl]-benzoyl]-2-oxo-6-phenyl-1,2-dihydro-pyridin-3-yl}-2-ethylamino-propionamide;
(S)—N-{1-[3-(4-Fluoro-phenylamino)-benzyl]-2-oxo-6-phenyl-1,2-dihydro-pyridin-3-yl}-2-methylamino-propionamide;
(S)—N-{1-[3-(4-Fluoro-phenylamino)-benzyl]-2-oxo-6-phenyl-1,2-dihydro-pyridin-3-yl}-2-ethylamino-propionamide;
(S)—N-{1-[3-(4-Fluoro-phenylamino)-benzoyl]-2-oxo-6-phenyl-1,2-dihydro-pyridin-3-yl}-2-ethylamino-propionamide;
(S)—N-(1-{3-[(4-Fluoro-phenyl)-methyl-amino]-benzyl}-2-oxo-6-phenyl-1,2-dihydro-pyridin-3-yl)-2-methylamino-propionamide;

(S)—N-(1-{3-[(4-Fluoro-phenyl)-methyl-amino]-benzoyl}-2-oxo-6-phenyl-1,2-dihydro-pyridin-3-yl)-2-methylamino-propionamide;

(S)—N-{1-[3-(4-Fluoro-phenylsulfanyl)-benzyl]-2-oxo-6-phenyl-1,2-dihydro-pyridin-3-yl}-2-methylamino-propionamide;

(S)—N-{1-[3-(4-Fluoro-benzenesulfonyl)-benzyl]-2-oxo-6-phenyl-1,2-dihydro-pyridin-3-yl}-2-methylamino-propionamide;

(S)—N-{1-[3-(4-Fluoro-phenylsulfanyl)-benzoyl]-2-oxo-6-phenyl-1,2-dihydro-pyridin-3-yl}-2-methylamino-propionamide;

(S)—N-{1-[3-(4-Fluoro-benzenesulfonyl)-benzoyl]-2-oxo-6-phenyl-1,2-dihydro-pyridin-3-yl}-2-methylamino-propionamide;

(S)—N-{1-[3-(4-Fluoro-phenoxy)-benzyl]-2-oxo-6-phenyl-1,2-dihydro-pyridin-3-yl}-2-methylamino-propionamide;

(S)—N-{1-[3-(4-Fluoro-phenoxy)-benzoyl]-2-oxo-6-phenyl-1,2-dihydro-pyridin-3-yl}-2-methylamino-propionamide;

(S)—N-[3-(4-Fluoro-phenoxy)-benzyl]-6-(4-fluoro-phenyl)-2-oxo-1,2-dihydro-pyridin-3-yl]-2-methylamino-propionamide;

(S)—N-[1-[3-(4-Fluoro-benzoyl)-benzyl]-6-(4-fluoro-phenyl)-2-oxo-1,2-dihydro-pyridin-3-yl]-2-methylamino-propionamide;

(S)—N-{6-(4-Fluoro-phenyl)-1-[3-(4-fluoro-phenylamino)-benzyl]-2-oxo-1,2-dihydro-pyridin-3-yl}-2-methylamino-propionamide;

(S)—N-(6-(4-Fluoro-phenyl)-1-{3-[(4-fluoro-phenyl)-methyl-amino]-benzyl}-2-oxo-1,2-dihydro-pyridin-3-yl)-2-methylamino-propionamide;

(S)—N-{6-(4-Fluoro-phenyl)-1-[3-(4-fluoro-phenylsulfanyl)-benzyl]-2-oxo-1,2-dihydro-pyridin-3-yl}--2-methylamino-propionamide;

(S)—N-[1-[3-(4-Fluoro-benzenesulfonyl)-benzyl]-6-(4-fluoro-phenyl)-2-oxo-1,2-dihydro-pyridin-3-yl]-2-methylamino-propionamide;

(S)—N-[1-(2,2-Diphenyl-ethylcarbamoyl)-methyl]-6-(4-fluoro-phenyl)-2-oxo-1,2-dihydro-pyridine-3-yl]-2-methylamino-propionamide;

(S)—N-[1-(Diphenethylcarbamoyl)-ymethyl]-6-(4-fluoro-phenyl)-2-oxo-1,2-dihydro-pyridin-3-yl]-2-methylamino-propionamide;

(S)—N-{6-(4-Fluoro-phenyl)-2-oxo-1-[(1,2,3,4-tetrahydro-naphthalen-1-ylcarbamoyl)-methyl]-1,2-dihydro-pyridin-3-yl}-2-methylamino-propionamide;

(S)-2-Methylamino-N-{2-oxo-6-phenyl-1-[(1,2,3,4-tetrahydro-naphthalen-1-ylcarbamoyl)-methyl]-1,2-dihydro-pyridin-3-yl}-propionamide;

(S)—N-{1-[(4-Fluoro-benzylcarbamoyl)-methyl]-2-oxo-6-phenyl-1,2-dihydro-pyridin-3-yl}-2-methylamino-propionamide;

(S)—N-[(4-Fluoro-benzylcarbamoyly)-methyl]-6-(4-fluoro-phenyl)-2-oxo-1,2-dihydro-pyridin-3-yl]-2-methylamino-propionamide;

(S)—N-{6-(4-Fluoro-phenyl)-2-oxo-1-[2-(1,2,3,4-tetrahydro-naphthalen-1-ylamino)-acetyl]-1,2-dihydro-pyridin-3-yl}-2-methylamino-propionamide;

(S)—N-[6-(4-Fluoro-phenyl)-2-oxo-1-(1,2,3,4-tetrahydro-naphthalen-1-ylaminooxalyl)-1,2-dihydro-pyridin-3-yl]-2-methylamino-propionamide;

(S)—N-{6-(4-Fluoro-phenyl)-2-oxo-1-[2-(1,2,3,4-tetrahydro-naphthalen-1-ylamino)-ethyl]-1,2-dihydro-pyridin-3-yl}-2-methylamino-propionamide;

(S)—N-[1-{2-[Ethyl-(1,2,3,4-tetrahydro-naphthalen-1-yl)-amino]-ethyl}-6-(4-fluoro-phenyl)-2-oxo-1,2-dihydro-pyridin-3-yl]-2-methylamino-propionamide;

(S)—N-[1-{[Ethyl-(1,2,3,4-tetrahydro-naphthalen-1-yl)-carbamoyl]-methyl}-6-(4-fluoro-phenyl)-2-oxo-1,2-dihydro-pyridin-3-yl]-2-methylamino-propionamide;

(S)—N-[1-{2-[Ethyl-(1,2,3,4-tetrahydro-naphthalen-1-yl)-amino]-acetyl}-6-(4-fluoro-phenyl)-2-oxo-1,2-dihydro-pyridin-3-yl]-2-methylamino-propionamide;

(S)—N-[1-{[Ethyl-(4-fluoro-benzyl)-carbamoyl]-methyl}-6-(4-fluoro-phenyl)-2-oxo-1,2-dihydro-pyridin-3-yl]-2-methylamino-propionamide;

(S)—N-1-{2-[Ethyl-(4-fluoro-benzyl)-amino]-ethyl}-6-(4-fluoro-phenyl)-2-oxo-1,2-dihydro-pyridin-3-yl]-2-methylamino-propionamide;

(S)—N-{1-[2-(Indan-2-yloxy)-ethyl]-2-oxo-6-phenyl-1,2-dihydro-pyridin-3-yl}-2-methylamino-propionamide;

(S)-N-{1-[2-(Indan-2-yloxy)-ethyl]-2-oxo-6-phenyl-1,2-dihydro-pyridin-3-yl}-2-methylamino-propionamide;

(S)-2-Methylamino-N-[2-oxo-1-(2-phenethylsulfanyl-ethyl)-6-phenyl-1,2-dihydro-pyridin-3-yl]-propionamide;

(S)-2-Methylamino-N-{2-oxo-6-phenyl-1-[2-(2-phenyl-ethanesulfonyl)-ethyl]-1,2-dihydro-pyridin-3-yl}-propionamide;

(S)-2-Methylamino-N-[2-oxo-6-phenyl-1-(5-phenyl-pentyl)-1,2-dihydro-pyridin-3-yl]-propionamide;

(S)—N-{1-[2-(1,3-Dihydro-isoindol -2-yl)-2-oxo-ethyl]-2-oxo-6-phenyl-1,2-dihydro-pyridin-3-yl}-2-methylamino-propionamide;

(S)—N-{1-[2-(1,3-Dihydro-isoindol -2-yl)-2-oxo-ethyl]-2-oxo-6-phenyl-1,2-dihydro-pyridin-3-yl}-2-methylamino- butyramide;

(S)—N-{1-[3-(4-Fluoro-benzoyl)-benzyl]-2-oxo-6-phenyl-1,2-dihydro-pyridin-3-yl}-2-methylamino-butyramide;

(S)—N-{1-[3-(4-Fluoro-benzoyl)-benzoyl]-2-oxo-6-phenyl-1,2-dihydro-pyridin-3-yl}-2-methylamino-butyramide;

(S)—N-{1-[3-(4-Fluoro-phenylamino)-benzyl]-2-oxo-6-phenyl-1,2-dihydro-pyridin-3-yl}-2-methylamino-butyramide;

(S)—N-(1-{3-[(4-Fluoro-phenyl)-methyl-amino]-benzyl}-2-oxo-6-phenyl-1,2-dihydro-pyridin-3-yl)-2-methylamino-butyramide;

(S)—N-{1-[3-(4-Fluoro-benzenesulfonyl)-benzyl]-2-oxo-6-phenyl-1,2-dihydro-pyridin-3-yl}-2-methylamino- butyramide;

(S)—N-{1-[3-(4-Fluoro-phenoxy)-benzyl]-2-oxo-6-phenyl-1,2-dihydro-pyridin-3-yl}-2-methylamino- butyramide;

(S)—N-[1-[3-(4-Fluoro-phenoxy)-benzyl]-6-(4-fluoro-phenyl)-2-oxo-1,2-dihydro-pyridin-3-yl]-2-methylamino-butyramide;

(S)—N-[1-[3-(4-Fluoro-benzoyl)-benzyl]-6-(4-fluoro-phenyl)-2-oxo-1,2-dihydro-pyridin-3-yl]-2-methylamino-butyramide;

(S)—N-(6-(4-Fluoro-phenyl)-1-{3-[(4-fluoro-phenyl)-methyl-amino]-benzyl}-2-oxo-1,2-dihydro-pyridine-3-yl)-2-methylamino- butyramide;

(S)—N-[1-[3-(4-Fluoro-benzenesulfonyl)-benzyl]-6-(4-fluoro-phenyl)-2-oxo-1,2-dihydro-pyridin-3-yl]-2-methylamino- butyramide;

(S)—N-{6-(4-Fluoro-phenyl)-2-oxo-1-[(1,2,3,4-tetrahydro-naphthalen-1-ylcarbamoyl)-methyl]-1,2-dihydro-pyridin-3-yl}-2-methylamino-butyramide;

(S)—N-1-[(4-Fluoro-benzylcarbamoyl)-methyl]-6-(4-fluoro-phenyl)-2-oxo-1,2-dihydro-pyridin-3-yl]-2-methylamino-butyramide;

(S)—N-{6-(4-Fluoro-phenyl)-2-oxo-1-[2-(1,2,3,4-tetrahydro-naphthalen-1-ylamino)-acetyl]-1,2-dihydro-pyridin-3-yl}-2-methylamino-butyramide;

(S)—N-[1-{[Ethyl-(1,2,3,4-tetrahydro-naphthalen-1-yl)-carbamoyl]-methyl}-6-(4-fluoro-phenyl)-2-oxo-1,2-dihydro-pyridin-3-yl]-2-methylamino-butyramide;

(S)—N-[1-{[Ethyl-(4-fluoro-benzyl)-carbamoyl]-methyl}-6-(4-fluoro-phenyl)-2-oxo-1,2-dihydro-pyridine-3-yl]-2-methylamino-butyramide;

(S)-N-{1-[2-(Indan-2-yloxy)-ethyl]-2-oxo-6-phenyl-1,2-dihydro-pyridin-3-yl}-2-methylamino-butyramide; and (S)-2-Methylamino-N-{2-oxo-6-phenyl-1-[2-(2-phenyl-ethanesulfonyl)-ethyl]-1,2-dihydro-pyridine-3-yl}-butyramide;

or a pharmaceutically acceptable salt thereof.

6. A pharmaceutical composition which comprises a pharmaceutically acceptable carrier and a therapeutically effective amount of a compound of formula (II) according to claim 1.

7. A process to prepare compound of formula (II) according to claim 1 comprising the steps of
   (a) coupling of an amine HXU with a t-Boc-L-amino acid or its derivative using a peptide coupling agent; and
   (b) removing t-Boc with trifluoroacetic acid.

8. The process according to claim 7, wherein the coupling agent is DCC/HOBt or HBTU/HOBt.

* * * * *